(12) United States Patent
Ramsay et al.

(10) Patent No.: US 10,342,760 B2
(45) Date of Patent: Jul. 9, 2019

(54) LIPID NANOPARTICLES FOR TRANSFECTION AND RELATED METHODS

(71) Applicant: The University of British Columbia, Vancouver (CA)

(72) Inventors: Euan Ramsay, Vancouver (CA); R. James Taylor, Vancouver (CA); Colin Walsh, Belmont, CA (US); Nathan M. Belliveau, Weymouth (CA); Pieter R. Cullis, Vancouver (CA); Timothy Leaver, Delta (CA); Andre Wild, Vancouver (CA)

(73) Assignee: THE UNIVERSITY OF BRITISH COLUMBIA, Vancouver (CA)

( * ) Notice: Subject to any disclaimer, the term of this patent is extended or adjusted under 35 U.S.C. 154(b) by 0 days.

(21) Appl. No.: 14/775,539

(22) PCT Filed: Mar. 14, 2014

(86) PCT No.: PCT/US2014/029116
§ 371 (c)(1),
(2) Date: Sep. 11, 2015

(87) PCT Pub. No.: WO2014/172045
PCT Pub. Date: Oct. 23, 2014

(65) Prior Publication Data
US 2016/0022580 A1 Jan. 28, 2016

Related U.S. Application Data

(60) Provisional application No. 61/798,495, filed on Mar. 15, 2013.

(51) Int. Cl.
| | |
|---|---|
| *A61K 31/575* | (2006.01) |
| *A61K 31/7088* | (2006.01) |
| *A61K 9/127* | (2006.01) |
| *C12N 15/88* | (2006.01) |
| *A61K 9/00* | (2006.01) |
| *A61K 31/713* | (2006.01) |
| *A61K 31/7105* | (2006.01) |
| *A61K 31/711* | (2006.01) |
| *A61K 47/32* | (2006.01) |
| *A61K 47/44* | (2017.01) |
| *A61K 9/51* | (2006.01) |

(52) U.S. Cl.
CPC ............ *A61K 9/127* (2013.01); *A61K 9/0019* (2013.01); *A61K 9/1277* (2013.01); *A61K 9/5123* (2013.01); *A61K 9/5192* (2013.01); *A61K 31/575* (2013.01); *A61K 31/7088* (2013.01); *A61K 31/711* (2013.01); *A61K 31/713* (2013.01); *A61K 31/7105* (2013.01); *A61K 47/32* (2013.01); *A61K 47/44* (2013.01); *C12N 15/88* (2013.01)

(58) Field of Classification Search
CPC .............. A61K 31/575; A61K 31/7088; A61K 31/7105; A61K 31/711; A61K 31/713; A61K 47/32; A61K 47/44; A61K 9/0019; A61K 9/127; A61K 9/1277; A61K 9/1278; A61K 9/5123; A61K 9/5192; C12N 15/88
USPC ................ 424/450; 435/375; 514/171, 44 A; 264/4.1
See application file for complete search history.

(56) References Cited

U.S. PATENT DOCUMENTS

| | | | |
|---|---|---|---|
| 5,921,678 A | 7/1999 | Desai et al. | |
| 5,981,501 A | 11/1999 | Wheeler et al. | |
| 6,479,299 B1 | 11/2002 | Parce et al. | |
| 6,534,018 B1 | 3/2003 | Baker | |
| 6,534,484 B1 | 3/2003 | Wheeler et al. | |
| 6,815,432 B2 | 11/2004 | Wheeler et al. | |
| 6,835,395 B1 | 12/2004 | Semple et al. | |
| 6,843,942 B2 | 1/2005 | Katlinger et al. | |
| 7,005,140 B2 | 2/2006 | Zhang | |
| 7,160,025 B2 | 1/2007 | Ji et al. | |
| 7,214,348 B2 | 5/2007 | Desmond et al. | |
| 7,252,928 B1 | 8/2007 | Hafeman et al. | |
| 7,341,738 B2 | 3/2008 | Semple et al. | |
| 7,422,902 B1 | 9/2008 | Wheeler et al. | |
| 7,507,380 B2 | 3/2009 | Chang et al. | |
| 7,622,509 B2 | 11/2009 | Tonkovich et al. | |
| 7,708,949 B2 | 5/2010 | Stone et al. | |

(Continued)

FOREIGN PATENT DOCUMENTS

| | | |
|---|---|---|
| CA | 2 427 640 A1 | 5/2003 |
| CA | 2 491 164 A1 | 1/2004 |

(Continued)

OTHER PUBLICATIONS

Leung et al. Journal of Physical Chemistry, C, VO.*
Abrams, M.T., et al., "Evaluation of Efficacy, Biodistribution, and Inflammation for a Potent siRNA Nanoparticle: Effect of Dexamethasone Co-Treatment," Molecular Therapy 18(1):171-180, Jan. 2010.
Avnir, Y., et al., Amphipathic Weak Acid Glucocorticoid Prodrugs Remote-Loaded Into Sterically Stabilized Nanoliposomes Evaluated in Arthritic Rats and in a Beagle Dog: A Novel Approach to Treating Autoimmune Arthritis, Arthritis & Rheumatism 58(1):119-129, Jan. 2008.

(Continued)

*Primary Examiner* — Janet L Epps-Smith
(74) *Attorney, Agent, or Firm* — Christensen O'Connor Johnson Kindness PLLC

(57) ABSTRACT

Transfection reagent composition, lipid nanoparticles prepared from the transfection reagent composition, kits that include the transfection reagent composition, and methods for making and using lipid nanoparticles prepared from the transfection reagent composition. Lipids when dispersed in aqueous media readily form liposomes, such as unilamellar vesicles and multilamellar vesicles. Liposomes have been used successfully to encapsulate and deliver a wide range of chemicals including nucleic acids, proteins and small molecule drugs, to cells.

1 Claim, 10 Drawing Sheets
Specification includes a Sequence Listing.

(56) References Cited

U.S. PATENT DOCUMENTS

| | | |
|---|---|---|
| 7,745,221 B2 | 6/2010 | Butler et al. |
| 7,794,136 B2 | 9/2010 | Yang et al. |
| 7,901,708 B2 | 3/2011 | MacLachlan et al. |
| 8,058,069 B2 | 11/2011 | Yaworski et al. |
| 8,106,176 B2 | 1/2012 | Aurisicchio et al. |
| 8,122,909 B2 | 2/2012 | Tonkovich et al. |
| 8,137,699 B2 | 3/2012 | Johnson et al. |
| 8,273,573 B2 | 9/2012 | Ismagilov et al. |
| 8,329,070 B2 | 12/2012 | MacLachlan et al. |
| 8,361,415 B2 | 1/2013 | Di Carlo et al. |
| 8,367,004 B2 | 2/2013 | Panagiotou et al. |
| 8,414,182 B2 | 4/2013 | Paul et al. |
| 8,492,359 B2 | 7/2013 | Yaworski et al. |
| 8,496,961 B2 | 7/2013 | Hong et al. |
| 8,522,413 B2 | 9/2013 | Van't Oever et al. |
| 8,883,200 B2 | 11/2014 | Hong et al. |
| 9,005,654 B2 | 4/2015 | MacLachlan et al. |
| 2003/0077829 A1 | 4/2003 | MacLachlan |
| 2004/0262223 A1 | 12/2004 | Strook et al. |
| 2006/0219307 A1 | 10/2006 | Wang et al. |
| 2007/0087045 A1 | 4/2007 | Li et al. |
| 2007/0263485 A1 | 11/2007 | Yang et al. |
| 2010/0022680 A1 | 1/2010 | Karnik et al. |
| 2011/0070292 A1 | 3/2011 | Javeri et al. |
| 2011/0091525 A1† | 4/2011 | Heyes |
| 2011/0182994 A1 | 7/2011 | Kornfield et al. |
| 2011/0262527 A1† | 10/2011 | Heyes |
| 2011/0305734 A1 | 12/2011 | Edelson et al. |
| 2011/0311582 A1† | 12/2011 | Manoharan |
| 2011/0311583 A1† | 12/2011 | Manoharan |
| 2012/0101148 A1* | 4/2012 | Aking ............... A61K 48/0008 514/44 A |
| 2012/0183602 A1* | 7/2012 | Chen .................. A61K 9/1272 424/450 |
| 2012/0270921 A1* | 10/2012 | de Fougerolles .. C12N 15/1131 514/44 A |
| 2012/0276209 A1* | 11/2012 | Cullis ................. A61K 9/1272 424/490 |
| 2013/0303587 A1 | 11/2013 | Yaworski et al. |

FOREIGN PATENT DOCUMENTS

| | | | |
|---|---|---|---|
| CA | 2 578 574 A1 | 2/2006 | |
| CA | 2 579 695 A1 | 3/2006 | |
| CA | 2 616 877 A1 | 2/2007 | |
| CA | 2 673 924 A1 | 7/2008 | |
| CA | 2 781 527 A1 | 3/2011 | |
| EP | 2 123 260 A1 | 11/2009 | |
| JP | 2005-525815 A | 9/2005 | |
| JP | 2007-252979 A | 4/2007 | |
| JP | 2007-513122 A | 5/2007 | |
| JP | 2007-524604 A | 8/2007 | |
| JP | 2007-533647 A | 11/2007 | |
| JP | 2008-526493 A | 7/2008 | |
| JP | 2009-509553 A | 3/2009 | |
| JP | 2010-514708 A | 5/2010 | |
| JP | 2013-510096 A | 3/2013 | |
| WO | 03/097805 A2 | 11/2003 | |
| WO | 2005/039535 A1 | 5/2005 | |
| WO | 2005/053642 A1 | 6/2005 | |
| WO | 2005/120152 A2 | 11/2005 | |
| WO | 2005/120461 A2 | 12/2005 | |
| WO | 2006/074336 A1 | 7/2006 | |
| WO | 2007/150030 A2 | 12/2007 | |
| WO | 2008/053988 A1 | 5/2008 | |
| WO | 2009/086558 A1 | 7/2009 | |
| WO | 2009/127060 A1 | 10/2009 | |
| WO | 2011/140627 A1 | 11/2011 | |
| WO | WO-2011140627 A1 * | 11/2011 | ........... A61K 9/1272 |
| WO | 2012/000104 A1 | 1/2012 | |
| WO | 2012/016184 A2 | 2/2012 | |
| WO | WO 2012016184 A2 * | 2/2012 | ........... C07C 229/12 |

OTHER PUBLICATIONS

Belliveau, N.M., et al., "Microfluidic Synthesis of Highly Potent Limit-Size Lipid Nanoparticles for In Vivo Delivery of siRNA," Molecular Therapy-Nucleic Acids 1(8):e37, Aug. 2012, 9 pages.

Chen, D., et al., "Rapid Discovery of Potent siRNA-Containing lipid Nanoparticles Enabled by Controlled Microfluidic Formulation," Journal of the American Chemical Society 134(16):6948-6951, Apr. 2012.

Crawford, R., et al., "Analysis of Lipid Nanoparticles by Cryo-EM for Characterizing siRNA Delivery Vehicles," International Journal of Pharmaceutics 403(1-2):237-244, Jan. 2011.

Deamer, D.W., and P.S. Uster, "Liposome Preparation: Methods and Mechanisms," in M.J. Ostra (ed.), "Liposomes," Marcel Dekker, New York, 1983, pp. 27-52.

Geusens, B., et al., "Ultradeformable Cationic Liposomes for Delivery of Small Interfering RNA (siRNA) Into Human Primary Melanocytes," Journal of Controlled Release 133(3):214-220, Feb. 2009.

Gindy, M.E., et al., "Mechanism of Macromolecular Structure Evolution in Self-Assembled Lipid Nanoparticles for siRNA Delivery," Langmuir 30(16):4613-4622, Apr. 2014.

Heyes, J., et al., "Lipid Encapsulation Enables the Effective Systemic Delivery of Polyplex Plasmid DNA," Molecular Therapy 15(4):713-720, Apr. 2007.

Hope, M.J., et al., "Generation of Multilamellar and Unilamellar Phospholipid Vesicles," Chemistry and Physics of Lipids 40(2-4):89-107, Jun.-Jul. 1986.

Jahn, A., et al., "Preparation of Nanoparticles by Continuous-Flow Microfluidics," Journal of Nanoparticle Research 10(6):925-934, Aug. 2008.

Jeffs, L.B., et al., "A Scalable, Extrusion-Free Method for Efficient Liposomal Encapsulation of Plasmid DNA," Pharmaceutical Research 22(3):362-372, Mar. 2005.

Johnson, B.K., and R.K. Prud'Homme, "Mechanism for Rapid Self-Assembly of Block Copolymer Nanoparticles," Physical Review Letters 91(11):118302-1-118302-4, Sep. 2003.

Kapoor, M., et al., "Physicochemical Characterization Techniques for Lipid Based Delivery Systems for siRNA," International Journal of Pharmaceutics 427(1):35-57, May 2012.

Karnik, R., et al., "Microfluidic Platform for Controlled Synthesis of Polymeric Nanoparticles," Nano Letters 8(9):2906-2912, Sep. 2008.

Koh, C.G., et al., "Delivery of Antisense Oligodeoxyribonucleotide Lipopolyplex Nanoparticles Assembled by Microfluidic Hydrodynamic Focusing," Journal of Controlled Release 141(1):62-69, Jan. 2010.

MacLachlan, I., "Liposomal Formulations for Nucleic Acid Delivery," in S.T. Crooke (ed.), "Antisense Drug Technology: Principles, Strategies, and Applications," 2nd ed., Chap. 9, CRC Press, Jul. 2007.

Montana, G., et al., "Employment of Cationic Solid-Lipid Nanoparticles as RNA Carriers," Bioconjugate Chemistry 18:302-308, Published on Web Jan. 25, 2007.

Peer, D., and R. Margalit, "Tumor-Targeted Hyaluronan Nanoliposomes Increase the Antitumor Activity of Liposomal Doxorubicin in Syngeneic and Human Xenograft Mouse Tumor Models," Neoplasia 6(4):343-353, Jul.-Aug. 2004.

Rudra, A., et al., "Doxorubicin-Loaded Phosphatidylelhanolamine-Conjugated Nanoliposomes: In Vitro Characterization and Their Accumulation in Liver, Kidneys, and Lungs in Rats," International Journal of Nanomedicine 5:811-823, Oct. 2010.

Seo, M., et al., "Microfluidic Assembly of Monodisperse, Nanoparticle-Incorporated Perfluorocarbon Microbubbles for Medical Imaging and Therapy," Langmuir 26(17):13855-13860, Published on Web Jul. 28, 2010.

Szoka, F., Jr., "Comparative Properties and Methods of Preparation of Lipid Vesicles (Liposomes)," Annual Review of Biophysics and Bioengineering 9:467-508, 1980.

Vemuri, S., and C.T. Rhodes, "Preparation and Characterization of Liposomes as Therapeutic Delivery Systems: A Review," Pharmaceutica Acta Helvetiae 70(2):95-111, Jul. 1995.

(56) References Cited

OTHER PUBLICATIONS

Xu, Y., et al., "Physicochemical Characterization and Purification of Cationic Lipoplexes," Biophysical Journal 77(1):341-353, Jul. 1999.
Yu, B., et al., "Microfluidic Methods for Production of Liposomes," Methods in Enzymology 465:129-141, 2009.
Zhang, J., et al., "Assessing the Heterogeneity Level in Lipid Nanoparticles for siRNA Delivery: Size-Based Separation, Composition at Heterogeneity, and Impact of Bioperformance," Molecular Pharmaceutics 10(1):397-405, Jan. 2013.
Zhang J. et al., "Polydispersity Characterization of Lipid Nanoparticles for siRNA Delivery Using Multiple Detection Size-Exclusion Chromatography," Analytical Chemistry 84(14):6088-6096, Jul. 2012.
Zhigaltsev, I.V., et al., "Bottom-Up Design and Synthesis of Limit Size Lipid Nanoparticle Systems With Aqueous and Triglyceride Cores Using Millisecond Microfluidic Mixing," Langmuir 28(7):3633-3640, Feb. 2012.
First Office Action dated Jul. 15, 2014, issued in Japanese Patent Application No. 2012-537274, filed Nov. 4, 2010, 5 pages.
Decision of Rejection dated Apr. 7, 2015 (with foreign associate's comments), issued in Japanese Application No. 2012-537274, filed Nov. 4, 2010, 6 pages.
International Search Report and Written Opinion dated Feb. 8, 2011, issued in International Application No. PCT/CA2010/001766, filed Nov. 4, 2010, 17 pages.
International Preliminary Report on Patentability dated May 18, 2012, issued in International Application No. PCT/CA2010/001766, filed Nov. 4, 2010, 11 pages.
International Search Report dated Feb. 18, 2013, issued in International Application No. PCT/CA2012/000991, filed Oct. 25, 2012, 18 pages.
Notification of the Second Office Action, dated Jan. 24, 2014, in Chinese Application No. 201080059999.7, filed Nov. 4, 2010, 7 pages.
Notification of the Third Office Action, dated Oct. 15, 2014, issued in Chinese Application No. 201080059999.7, filed Nov. 4, 2010, 7 pages.
Notification of the Fourth Office Action dated Jul. 6, 2015, issued in Chinese Application No. 201080059999.7, filed Nov. 4, 2010, 10 pages.
Office Action dated Oct. 10, 2014, issued in Russian Application No. 2012122776, filed Nov. 4, 2010, 12 pages.
Partial Supplementary European Search Report dated Jun. 1, 2015, issued in corresponding European Application No. 12843980.9, filed Oct. 25, 2012, 5 pages.
Extended European Search Report dated Oct. 6, 2015, issued in corresponding European Application No. 12843980.9, filed Oct. 25, 2012, 7 pages.
Supplementary European Search Report dated Dec. 6, 2013, issued in European Application No. 10 85 1175.9, filed Nov. 4, 2010, 10 pages.
Communication Pursuant to Article 94(3) EPC, dated Jul. 18, 2014, in European Application No. 10 85 1175.9, filed Nov. 4, 2010, 7 pages.
Extended European Search Report dated Jul. 8, 2016, issued in European Patent Application No. 16166730.8, filed Oct. 25, 2012, 6 pages.
First Office Action dated Jul. 20, 2016, issued in Japanese Application No. 2014-537433, filed Oct. 25, 2012, 8 pages.
Notification of the Fifth Office Action, dated Mar. 28, 2016, issued in corresponding Chinese Application No. 201080059999.7, filed Nov. 4, 2010, 9 pages.
First Office Action dated Jul. 5, 2016, issued in Japanese Application No. 2015-157385, filed Aug. 7, 2015, 5 pages.
Notification of the Sixth Office Action, dated Sep. 30, 2016, issued in corresponding Chinese Application No. 201090059999.7, filed Nov. 4, 2010, 7 pages.
Maurer, N., et al., "Spontaneous Entrapment of Polynucleotides Upon Electrostatic Interaction With Ethanol-Destablized Cationic Liposomes," Biophysical Journal 80(5):2310-2326, May 2001.
Extended European Search Report dated Sep. 21, 2016, issued in International Application No. 14785963.1, filed Mar. 14, 2014, 7 pages.
Leung, A.K., et al., Lipid Nanoparticles Containing siRNA synthesized by Microfluidic Mixing Exhibit an Electron-Dense Nanostructured Core, The Journal of Physical Chemistry, C, Nanomaterials and Interfaces 116(34):18440-18450, Aug. 2012.
International Preliminary Report on Patentability dated Sep. 15, 2015, issued in corresponding International Application No. PCT/US2014/029116, filed Mar. 14, 2014, 6 pages.
International Search Report and Written Opinion, dated Jul. 29, 2014, issued in corresponding International Application No. PCT/US2014/029116, filed Mar. 14, 2014, 13 pages.
Chinese Office Action dated Apr. 26, 2018, issued in corresponding Chinese Application No. 201480022785.0, filed Mar. 14, 2014, 17 pages.
Masahito Miyamoto et al., Preparation of Gadolinium-Containing Emulsions Stabilized with Phosphatidylcholine-Surfacant Mixtures for Neutron-Capture Therapy, Chem. Pharm. Bull, Feb. 1999, p. 203-208, vol. 47 No. 2, Japan.
First Office Action dated May 22, 2018, issued in corresponding Japanese Application No. JP/2016/502968, Filed Mar. 14, 2014, 11 pages.
Communication Pursuant to Article 94(3)EPC, dated Feb. 21, 2018, issued in corresponding European Application No. 14785963.1, filed Mar. 14, 2014, 7 pages.
Bunjes, Heike et al., "Effects of Surfactants on the Crystallization and Polymorphism of Lipid Nanoparticles," Progr Colloid Polym Sci (2002) 121: 7-10, 4 Pages.
Carbone, C. et al., "Preparation and Optimization of PIT Solid Lipid Nanoparticles via Statistical Factorial Design," European Journal of Medicinal Chemistry 49 (2012), pages 110-117.
Khan, Shagufta et al., "Preformulation Studies and Preperation of Dithranol Loaded Solid Lipid Nanoparticles," International Journal of Research and Decelopment in Pharmacy and Life Sciences, vol. 1 No. 4, (2012), Pages 183-188.
First Office Action dated Jan. 29, 2019, issued in corresponding Japanese Application No. 2016-502986, filed Mar. 14, 2014, 6 pages.
Communication Pursuant to Article 94(3) EPC dated Mar. 25, 2019, issued in corresponding European Application No. 14785963.1, filed Mar. 14, 2014, 6 pages.

\* cited by examiner
† cited by third party

Table 1

| Formulation (Cationic Lipid A:DSPC:Chol:Surfactant) | Surfactant | Sample Name | Z-Ave (d.nm) | StDev | PDI |
|---|---|---|---|---|---|
| 50:10:39:1 | Myrj 52 | LNP-Myrj 52 1% | 103.2 | 1.2 | 0.13 |
| 50:10:37.5:2.5 | Myrj 52 | LNP-Myrj 52 2.5% | 72.2 | 0.6 | 0.16 |
| 50:10:35:5 | Myrj 52 | LNP-Myrj 52 5% | 48.7 | 0.4 | 0.08 |
| 50:10:38:2 | Brij 98 | LNP-BRIJ 98 2% | 92.6 | 0.9 | 0.06 |
| 50:10:35:5 | Brij 98 | LNP-BRIJ 98 5% | 67.6 | 1.0 | 0.11 |
| 50:10:38:2 | Brij 35P | LNP-BRIJ 35P 2% | 111.7 | 1.9 | 0.05 |
| 50:10:35:5 | Brij 35P | LNP-BRIJ 35P 5% | 72.5 | 0.4 | 0.15 |
| 50:10:30:10 | Brij 35P | LNP-BRIJ 35P 10% | 56.4 | 0.8 | 0.11 |

*Fig. 6*

Table 2

| Formulation (Cationic Lipid A:DSPC:Chol:Surfactant) | Surfactant | Sample Name | % Encapsulation |
|---|---|---|---|
| 50:10:39:1 | Myrj 52 | LNP-Myrj 52 1% | 97.7 |
| 50:10:37.5:2.5 | Myrj 52 | LNP-Myrj 52 2.5% | 96.3 |
| 50:10:35:5 | Myrj 52 | LNP-Myrj 52 5% | 94.5 |
| 50:10:38:2 | Brij 98 | LNP-BRIJ 98 2% | 97.2 |
| 50:10:35:5 | Brij 98 | LNP-BRIJ 98 5% | 97.0 |
| 50:10:38:2 | Brij 35P | LNP-BRIJ 35P 2% | 97.2 |
| 50:10:35:5 | Brij 35P | LNP-BRIJ 35P 5% | 98.2 |
| 50:10:30:10 | Brij 35P | LNP-BRIJ 35P 10% | 95.2 |

*Fig. 7*

LIPID NANOPARTICLES FOR TRANSFECTION AND RELATED METHODS

CROSS-REFERENCE TO RELATED APPLICATION

This application claims the benefit of U.S. Patent Application No. 61/798,495, filed Mar. 15, 2013, expressly incorporated herein by reference in its entirety.

STATEMENT REGARDING SEQUENCE LISTING

The sequence listing associated with this application is provided in text format in lieu of a paper copy and is hereby incorporated by reference into the specification. The name of the text file containing the sequence listing is 43935_Sequence_Final_2014-03-14.txt. The text file is 748 bytes; was created on Mar. 14, 2014; and is being submitted via EFS-Web with the filing of the specification.

BACKGROUND OF THE INVENTION

Lipids when dispersed in aqueous media readily form liposomes, such as unilamellar vesicles and multilamellar vesicles. Liposomes have been used successfully to encapsulate and deliver a wide range of chemicals including nucleic acids, proteins and small molecule drugs, to cells.

Cationic liposomes prepared from a composition of cationic lipids and phospholipids, readily form aggregates with anionic macromolecules such as DNA and RNA. These cationic liposome—nucleic acid aggregates are often engineered such that the net charge of the complex is positive, which is believed to facilitate interaction with the anionic cell surface thereby enhancing uptake of the encapsulated cargo and subsequent cell transfection. An example of a cationic lipid composition that is commonly used for the transfection of cells in vitro is N-[1-(2,3-dioleoyloxy)propyl]-N,N,N-trimethylammonium chloride (DOTMA) combined with dioleoylphosphatidylethanolamine (DOPE) at a molar ratio of 1:1.

The size and structure of cationic liposome—nucleic acid aggregate is dependent on the lipid composition and the method of manufacture. These structures can range in size from several hundred nanometers to micrometers and often have heterogeneous morphologies when visualized by electron microscopy, including the classic "spaghetti and meatballs" conformation.

Cationic liposome—nucleic acid aggregates have limited effectiveness in primary cells, i.e., cells harvested from a living organism. This is believed to be the result of toxicity due to excessive cationic charge. Toxicity plus large particle size also limits use of cationic liposome—nucleic acid aggregates for transfection in vivo.

Lipid nanoparticles (LNP) are the most clinically advanced drug delivery systems, with seven LNP-based drugs having received regulatory approval. These approved drugs contain small molecules such as anticancer drugs and exhibit improved efficacy and/or reduced toxicity compared to the "free" drug. LNP carrier technology has also been applied to delivery of "genetic" anionic macromolecules such as plasmids for protein expression or small interfering RNA (siRNA) oligonucleotides (OGN) for gene silencing.

Recent advances in LNP technology and the cationic lipids used to encapsulate and deliver of genetic drugs, have enabled siRNA-LNP that have been shown to overcome the inherent liabilities of cationic liposome—nucleic acid aggregates and mediate silencing of therapeutically relevant target genes in difficult-to-transfect primary cells and animal models, including non-human primates following intravenous (i.v.) injection. These siRNA-LNP are currently under evaluation in several clinical trials.

A variety of methods have been developed to formulate LNP systems containing genetic drugs. These methods include mixing preformed LNP with OGN in the presence of ethanol, or mixing lipid dissolved in ethanol with an aqueous media containing OGN, and result in LNP with diameters of 100 nm or less and OGN encapsulation efficiencies of 65-95%. Both of these methods rely on the presence of cationic lipid to achieve encapsulation of OGN and poly (ethylene glycol) (PEG) lipids to inhibit aggregation and the formation of large structures. The properties of the LNP systems produced, including size and OGN encapsulation efficiency, are sensitive to a variety of formulation parameters such as ionic strength, lipid and ethanol concentration, pH, OGN concentration and mixing rates. In general, parameters such as the relative lipid and OGN concentrations at the time of mixing, as well as the mixing rates are difficult to control using current formulation procedures, resulting in variability in the characteristics of LNP produced, both within and between preparations.

Microfluidic devices rapidly mix fluids at the nanoliter scale with precise control over temperature, residence times, and solute concentrations. Controlled and rapid microfluidic mixing has been previously applied in the synthesis of inorganic nanoparticles and microparticles, and can outperform macroscale systems in large-scale production of nanoparticles. Microfluidic two-phase droplet techniques have been applied to produce monodisperse polymeric microparticles for drug delivery or to produce large vesicles for the encapsulation of cells, proteins, or other biomolecules. The use of hydrodynamic flow focusing, a common microfluidic technique to provide rapid mixing of reagents, to create monodisperse liposomes of controlled size has been demonstrated. This technique has also proven useful in the production of polymeric nanoparticles where smaller, more monodisperse particles were obtained, with higher encapsulation of small molecules as compared to bulk production methods.

Despite the numerous products available for cell transfection, a need exists for devices and methods for the efficient delivery of siRNA OGN and other anionic macromolecules to difficult-to-transfect primary cells in vitro and to target cells in vivo. The present invention seeks to fulfill this need and provides further related advantages to address a major problem impeding the validation of aberrant genes, identified through genome sequencing of disease cells, as potential drug or biomarker targets.

SUMMARY OF THE INVENTION

In one aspect, the invention provides a transfection reagent composition comprising lipids and surfactants.

In one embodiment, the transfection reagent comprises (a) one or more cationic lipids, (b) one or more second lipids, and (c) one or more sterols, and (d) one or more surfactants.

In one embodiment, the cationic lipid is 1,17-bis(2-octylcyclopropyl)heptadecan-9-yl-4-(dimethylamino)butanoate. In certain embodiments, the particle comprises from about 30 to about 95 mole percent cationic lipid.

In one embodiment, the second lipid is 1,2-distearoyl-sn-glycero-3-phosphocholine (DSPC).

In one embodiment, the sterol is cholesterol.

In one embodiment, the surfactant is polyoxyethylene (20) oleyl ether. In a further embodiment, the surfactant is polyoxyethylene (40) stearate. In certain embodiments, the particle comprises from about 0.1 to about 20 mole percent surfactant.

In another embodiment, the lipid nanoparticle comprises (a) one or more cationic lipids, (b) one or more second lipids, (c) one or more sterols, and (d) one or more surfactants; as defined herein. In one embodiment, the cationic lipid is 1,17-bis(2-octylcyclopropyl)heptadecan-9-yl-4-(dimethylamino)butanoate. In one embodiment, the second lipid is 1,2-distearoyl-sn-glycero-3-phosphocholine (DSPC). In one embodiment, the sterol lipid is cholesterol. In one embodiment, the surfactant is polyoxyethylene (20) oleyl ether.

In another embodiment, the lipid nanoparticle comprises (a) one or more cationic lipids, (b) one or more second lipids, (c) one or more sterols, and (d) one or more surfactants; as defined herein. In one embodiment, the cationic lipid is 1,17-bis(2-octylcyclopropyl)heptadecan-9-yl-4-(dimethylamino)butanoate. In one embodiment, the second lipid is 1,2-distearoyl-sn-glycero-3-phosphocholine (DSPC). In one embodiment, the sterol lipid is cholesterol. In one embodiment, the surfactant is Polyoxyethylene (40) stearate.

In other aspects, the invention provides a lipid nanoparticle comprising a transfection reagent composition and an anionic macromolecule, wherein the lipid nanoparticle comprises a substantially solid core, as defined herein.

In one embodiment, the invention provides a lipid nanoparticle comprising a transfection reagent composition and a nucleic acid. The nucleic acid can be a DNA, a RNA, a locked nucleic acid, a nucleic acid analog, or a plasmid capable of expressing a DNA or an RNA.

In another embodiment, the invention provides a lipid nanoparticle comprising a transfection reagent composition and an antisense oligonucleotide hybridization probe. The hybridization probe can be a molecular beacon.

In another aspect, the invention provides a lipid nanoparticle comprising (a) one or more cationic lipids, (b) one or more second lipids, (c) one or more sterols, and (d) one or more surfactants and one or more nucleic acids as defined herein. In one embodiment, the cationic lipid is 1,17-bis(2-octylcyclopropyl)heptadecan-9-yl -4-(dimethylamino)butanoate. In one embodiment, the second lipid is 1,2-distearoyl-sn -glycero-3-phosphocholine (DSPC). In one embodiment, the sterol lipid is cholesterol. In one embodiment, the surfactant is polyoxyethylene (20) oleyl ether. In one embodiment the nucleic acid is a siRNA.

In another aspect, the invention provides a lipid nanoparticle comprising (a) one or more cationic lipids, (b) one or more second lipids, (c) one or more sterols, and (d) one or more surfactants and one or more nucleic acids as defined herein. In one embodiment, the cationic lipid is 1,17-bis(2-octylcyclopropyl)heptadecan-9-yl -4-(dimethylamino)butanoate. In one embodiment, the second lipid is 1,2-distearoyl-sn -glycero-3-phosphocholine (DSPC). In one embodiment, the sterol lipid is cholesterol. In one embodiment, the surfactant is polyoxyethylene (40) stearate. In one embodiment the nucleic acid is a siRNA.

In another aspect, the invention provides a lipid nanoparticle comprising (a) one or more cationic lipids, (b) one or more second lipids, (c) one or more sterols, and (d one or more surfactants and one or more nucleic acids as defined herein. In one embodiment, the cationic lipid is 1,17-bis(2-octylcyclopropyl)heptadecan-9-yl 4-(dimethylamino)butanoate. In one embodiment, the second lipid is 1,2-distearoyl-sn -glycero-3-phosphocholine (DSPC). In one embodiment, the sterol lipid is cholesterol. In one embodiment, the surfactant is polyoxyethylene (20) oleyl ether. In one embodiment the nucleic acid is a plasmid DNA.

In another aspect, the invention provides a lipid nanoparticle comprising (a) one or more cationic lipids, (b) one or more second lipids, (c) one or more sterols, and (d) one or more surfactants and one or more nucleic acids as defined herein. In one embodiment, the cationic lipid is 1,17-bis(2-octylcyclopropyl)heptadecan-9-yl -4-(dimethylamino)butanoate. In one embodiment, the second lipid is 1,2-distearoyl-sn -glycero-3-phosphocholine (DSPC). In one embodiment, the sterol lipid is cholesterol. In one embodiment, the surfactant is polyoxyethylene (40) stearate. In one embodiment the nucleic acid is a plasmid DNA.

In one embodiment, the invention provides a method for administering a nucleic acid to a subject, comprising administering a lipid nanoparticle of the invention to a subject in need thereof.

In one embodiment, the invention provides a method for introducing a nucleic acid into a cell, comprising contacting a cell with the lipid nanoparticle of the invention.

In one embodiment, the invention provides a method for modulating the expression of a target polynucleotide or polypeptide, comprising contacting a cell with the lipid nanoparticle of the invention, wherein the nucleic acid capable of modulating the expression of a target polynucleotide or polypeptide.

In one embodiment, the invention provides a method of treating a disease or disorder characterized by overexpression of a polypeptide in a subject, comprising administering to the subject the lipid nanoparticle of the invention, wherein the nucleic acid capable of silencing or decreasing the expression of the polypeptide.

In one embodiment, the invention provides a method of treating a disease or disorder characterized by the absence of expression, or under expression, of a polypeptide in a subject, comprising administering to the subject the lipid nanoparticle of the invention, wherein the nucleic acid capable of expressing or increasing the expression of the polypeptide.

In other aspect, the invention provides a method for making lipid nanoparticles. In one embodiment, the invention provides a method for making lipid nanoparticles containing a nucleic acid, comprising:

(a) introducing a first stream comprising a nucleic acid in a first solvent into a microfluidic device; wherein the device has a first region adapted for flowing one or more streams introduced into the device and a second region for mixing the contents of the one or more streams with a microfluidic mixer;

(b) introducing a second stream comprising transfection reagent composition in a second solvent into the device, wherein the device has a first region adapted for flowing one or more streams introduced into the microchannel and directing them into a second region for mixing the contents of the one or more streams, wherein the transfection reagent composition comprise a cationic lipid, and wherein the first and second solvents are not the same;

(c) flowing the one or more first streams and the one or more second streams from the first region of the device into the second region of the device; and (d) mixing of the contents of the one or more first streams and the one or more second streams in the second region of the device to provide a third stream comprising lipid nanoparticles with encapsulated nucleic acid.

In another embodiment, the invention provides a method for making lipid nanoparticles containing a nucleic acid, comprising:

(a) introducing a first stream comprising a nucleic acid in a first solvent into a channel; wherein the device has a first region adapted for flowing one or more streams introduced into the channel and a second region for mixing the contents of the one or more streams;

(b) introducing a second stream comprising transfection reagent composition in a second solvent; wherein the channel has a first region adapted for flowing one or more streams introduced into the channel and a second region for mixing the contents of the one or more streams;

(c) flowing the one or more first streams and the one or more second streams from the first region of the channel into the second region of the channel, while maintaining a physical separation of the two streams, wherein the one or more first streams and the one or more second streams do not mix until arriving at the second region of the channel; and (d) mixing of the contents of the one or more first streams and the one or more second streams flowing in the second region of the microchannel to provide a third stream comprising lipid nanoparticles with encapsulated nucleic acids.

In certain embodiments of the above methods, mixing the contents of the one or more first streams and the one or more second streams comprises varying the concentration or relative mixing rates of the one or more first streams and the one or more second streams.

In certain embodiments of the above methods, the methods further comprise diluting the third stream with an aqueous buffer. In certain embodiments, diluting the third stream comprises flowing the third stream and an aqueous buffer into a second mixing structure.

In certain embodiments of the above methods, the methods further comprise dialyzing the aqueous buffer comprising lipid nanoparticles with encapsulated nucleic acids to reduce the amount of the second solvent.

In certain embodiments of the above methods, the first solvent is an aqueous buffer. In certain embodiments of the above methods, the second solvent is an aqueous alcohol.

In certain embodiments of the above methods, mixing the contents of the first and second streams comprises chaotic advection. In certain embodiments of the above methods, mixing the contents of the first and second streams comprises mixing with a micromixer.

In certain embodiments of the above methods, the nucleic acid encapsulation efficiency is from about 80 to about 100%.

In certain embodiments of the above methods, mixing of the one or more first streams and the one or more second streams is prevented in the first region by a barrier. In certain embodiments, the barrier is a channel wall, sheath fluid, or concentric tubing.

In another aspect of the invention, devices for making lipid nanoparticles are provided. In one embodiment, the invention provides a device for producing a lipid nanoparticle encapsulating a nucleic acid, comprising:

(a) a first inlet for receiving a first solution comprising a nucleic acid in a first solvent;

(b) a first inlet microchannel in fluid communication with the first inlet to provide a first stream comprising the nucleic acid in the first solvent;

(c) a second inlet for receiving a second solution comprising transfection reagent composition in a second solvent;

(d) a second inlet microchannel in fluid communication with the second inlet to provide a second stream comprising the transfection reagent composition in the second solvent; and (e) a third microchannel for receiving the first and second streams, wherein the third microchannel has a first region adapted for flowing the first and second streams introduced into the microchannel and a second region adapted for mixing the contents of the first and second streams to provide a third stream comprising lipid nanoparticles with encapsulated nucleic acid.

In one embodiment, the device further comprises means for diluting the third stream to provide a diluted stream comprising stabilized lipid nanoparticles with encapsulated nucleic acid. In certain embodiments, the means for diluting the third stream comprises a micromixer.

In one embodiment, the microchannel has a hydrodynamic diameter from about 20 to about 300 μm.

In one embodiment, the second region of the microchannel comprises bas-relief structures. In one embodiment, the second region of the microchannel has a principal flow direction and one or more surfaces having at least one groove or protrusion defined therein, the groove or protrusion having an orientation that forms an angle with the principal direction. In one embodiment, the second region comprises a micromixer.

In certain embodiments, the device further comprises means for varying the flow rates of the first and second streams.

In certain embodiments, the device further comprises a barrier effective to physically separate the one or more first streams from the one or more second streams in the first region.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

siRNA-LNP were manufactured using the microfluidic method. Activity was measured as percent Residual FVII protein level as a function of siRNA dose and time. All LNP comprised: 1,17-bis(2-octylcyclopropyl)heptadecan-9-yl-4-(dimethylamino)butanoate: DSPC:Cholesterol:polyoxyethylene (40) stearate (50:10:37.5:2.5 mol %). siRNA-LNP-to-lipid ratio was 0.06 weight/weight. Mice (n=3) were injected via the tail vein with a single dose equivalent to 0.01, 0.05, 0.1, 0.3, 0.5 and 1 mg/kg siRNA. Blood collection was performed at days 1, 7, 14 and 21 post-injection and FVII levels were determined by colorimetric assay. The data indicates that FVII levels in the blood were reduced by >95% compared to for at least 7 days after a single intravenous injection of siRNA-LNP at a siRNA dose of 1 mg/kg.

Figure 3:
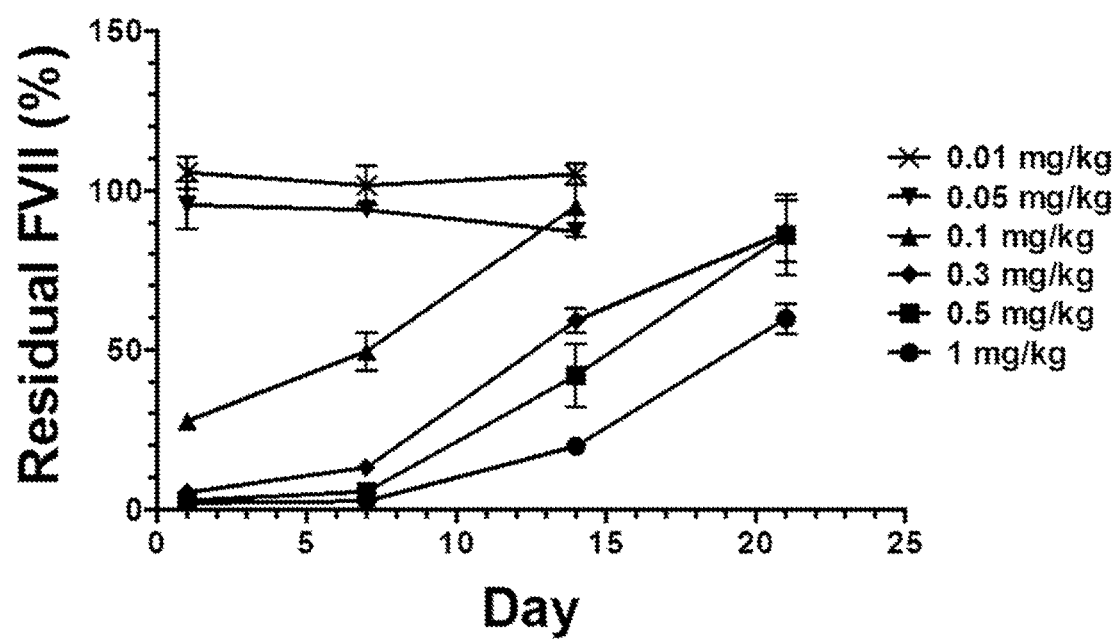

FIG. 3 uses the Factor VII (FVII) Mouse Model to illustrate the in vivo silencing activity of siRNA-LNP prepared with the surfactant polyoxyethylene (20) oleyl ether. siRNA-LNP were manufactured using the microfluidic method. Activity was measured as percent Residual FVII protein level as a function of siRNA dose and time. All LNP comprised: 1,17-bis(2-octylcyclopropyl)heptadecan-9-yl-4 (dimethylamino)butanoate: DSPC: Cholesterol: Polyoxyethylene (20) oleyl ether (50:10:38:2 mol %). siRNA-LNP-to-lipid ratio was 0.06 weight/weight. Mice (n=3) were injected via the tail vein with a single dose equivalent to 0.01, 0.05, 0.1, 0.3, 0.5 and 1 mg/kg siRNA. Blood collection was performed at days 1, 7, 14 and 21 post-injection and FVII levels were determined by colorimetric assay. The data indicates that FVII levels in the blood were reduced by >95% compared to for at least 7 days after a single intravenous injection of siRNA-LNP at a siRNA dose of >0.5 mg/kg.

Figure 4:
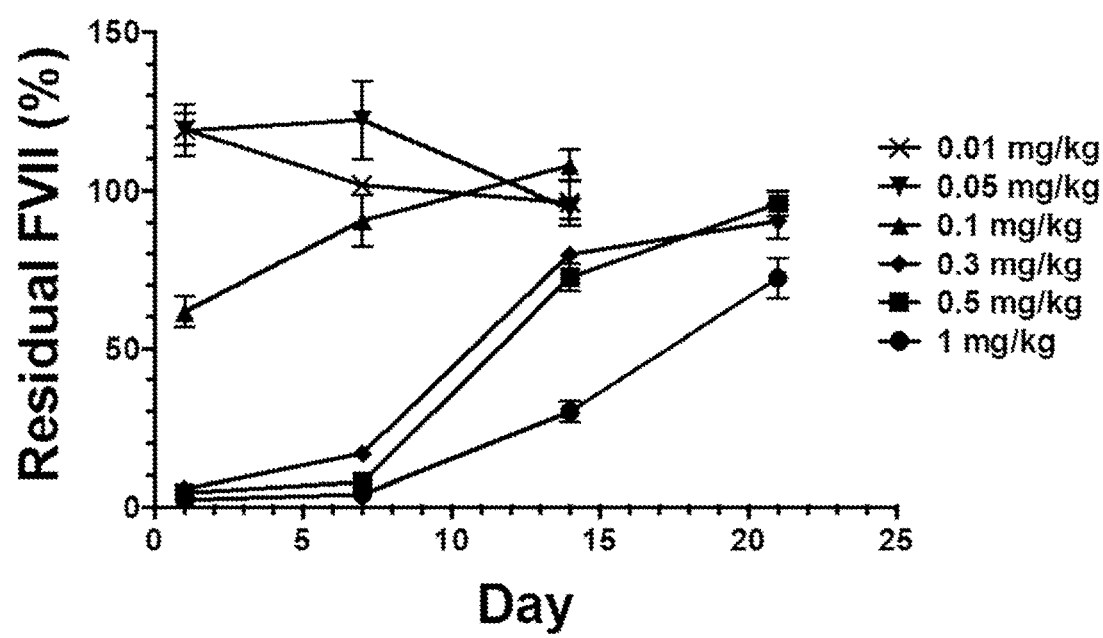

FIG. 4 uses the Factor VII (FVII) Mouse Model to illustrate the in vivo silencing activity of siRNA-LNP prepared with the surfactant polyoxyethylene (23) lauryl ether. siRNA-LNP were manufactured using the microfluidic method. Activity was measured as percent Residual FVII protein level as a function of siRNA dose and time. All LNP comprised: 1,17-bis(2-octylcyclopropyl)heptadecan-9-yl-4-(dimethylamino)butanoate: DSPC: Cholesterol: polyoxyethylene (23) lauryl ether(50:10:38:2 mol %). siRNA-LNP-to-lipid ratio was 0.06 wt/wt. Mice (n=3) were injected via the tail vein with a single dose equivalent to 0.01, 0.05, 0.1, 0.3, 0.5 and 1 mg/kg siRNA. Blood collection was performed at days 1, 7, 14 and 21 post-injection and FVII levels were determined by colorimetric assay. The data indicates that FVII levels in the blood were reduced by >95% compared to for at least 7 days after a single intravenous injection of siRNA-LNP at a siRNA dose of ≥0.5 mg/kg.

Figure 5:
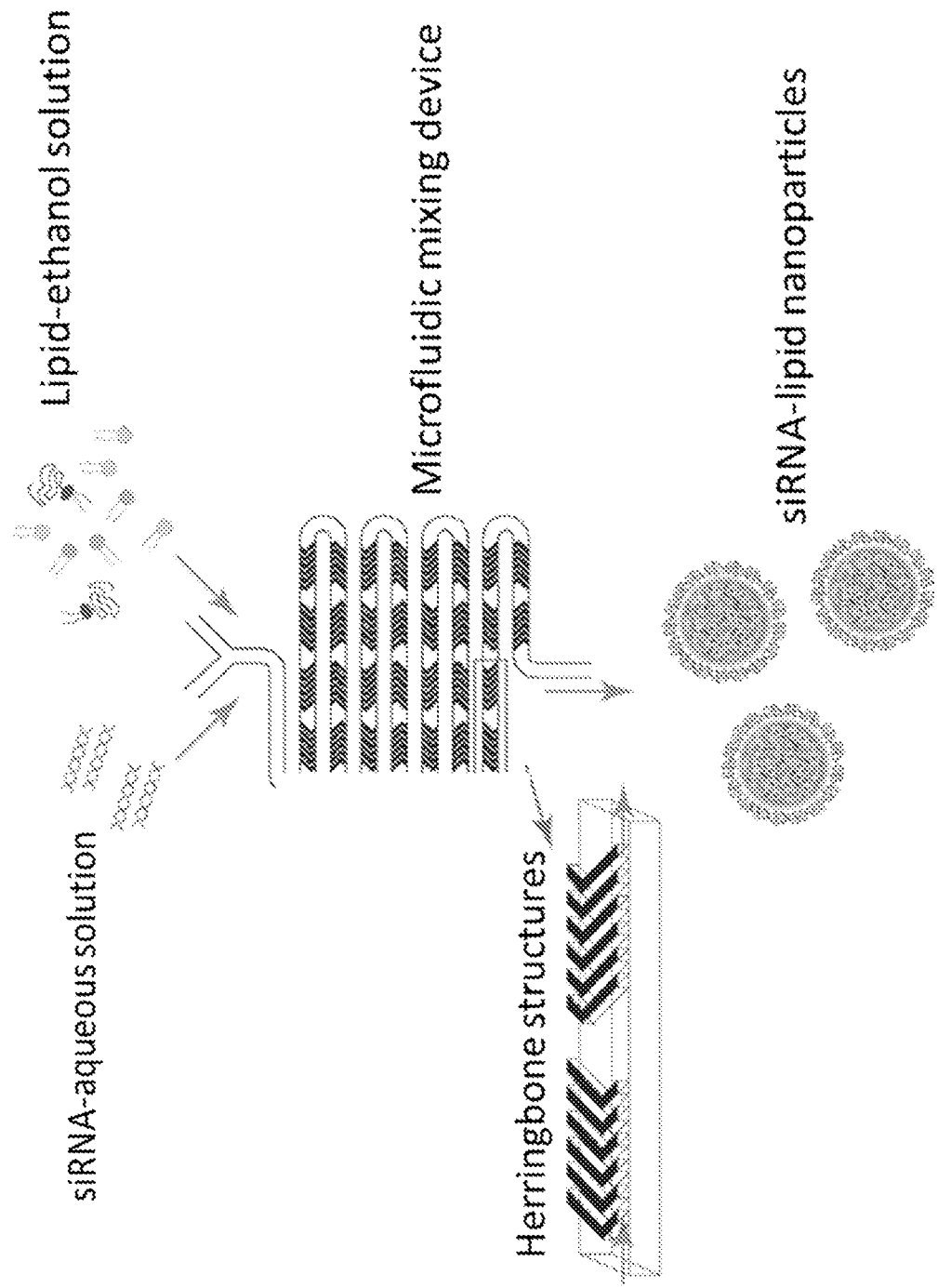

FIG. 5 is a schematic illustration of a representative microfluidic (MF) method of the invention for making lipid nanoparticles (LNP): Lipid-ethanol and siRNA-aqueous solutions are pumped into inlets of a microfluidic mixing device; herringbone features in the device induce chaotic advection of the stream and cause the lipid species to rapidly mix with the aqueous stream and form lipid nanoparticles. The mixing channel is 300 μm wide and 130 μm high. The herringbone structures are 40 μm high and 53 μm thick.

FIG. 6 is a table that summarizes Z-Ave and PDI for representative lipid nanoparticles prepared from transfection reagent compositions of the invention.

FIG. 7 is a table that summarizes nucleic acid encapsulation efficiency for representative lipid nanoparticles prepared from transfection reagent compositions of the invention.

Figure 8:
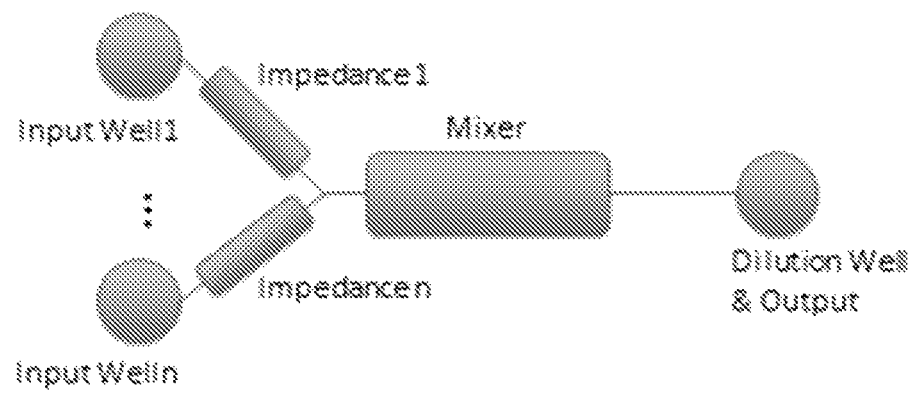

FIG. 8 is a schematic illustration of a representative device and method of the invention for preparing particles at small volumes: a device that uses a combination of input and output reservoirs (wells) to control flow rates and flow timing. In this device, input wells are used to contain input fluids. Channel impedances are used to determine the relative flow rates between flows from the inputs. An outlet well is added. In certain embodiments, a backpressure or stopper is applied to the outlet well to stop fluidic movement from the inputs due to the weight of fluids in the input wells or other phenomena, prior to a pressure applied to the inputs. In certain embodiments, a backpressure is achieved by adding fluid to the outlet well prior to adding fluids to the input wells. In this case fluids with the lowest surface tension are added last because these are the fluids which move through the chip at the highest rate. The input fluids are then added into the input reservoirs and the inputs are pressurized to create fluid flow. Flow rates of the different flows are controlled by the impedances of the channels from the inputs to the mixer chamber. The flows can be timed to reach the mixer at a similar time by pressurizing the input wells simultaneously. In certain embodiments, the device is purged of remaining fluid by applying fluid (gas or liquid) to the inputs and flowed through the mixers following nanoparticle manufacture.

Figure 9:
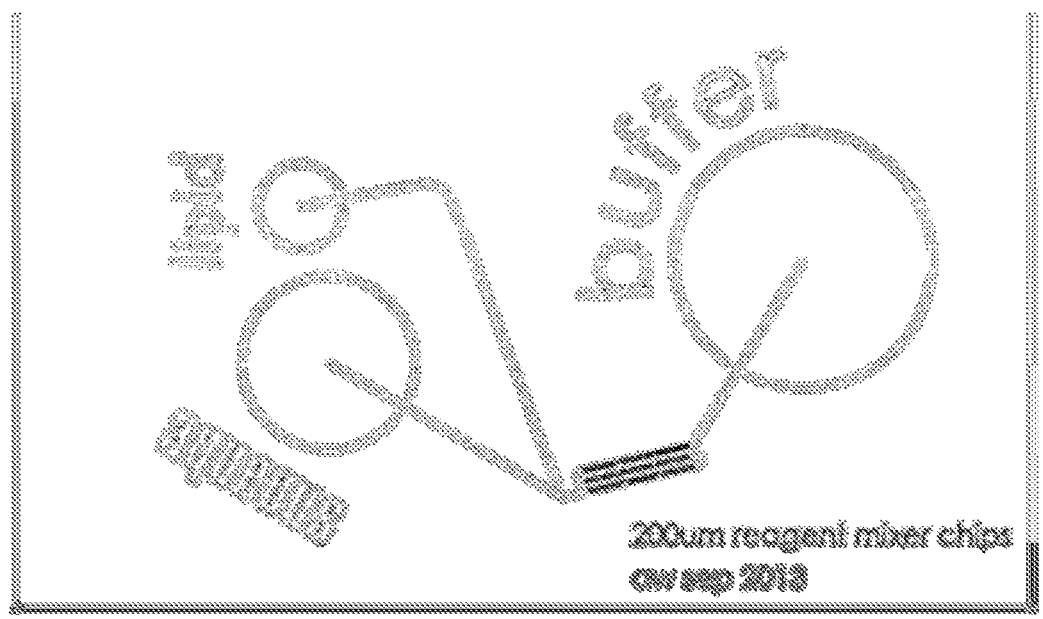

FIG. 9 is an example of a representative device illustrated in the schematic of FIG. 8. This device has two inlet wells (one for an aqueous phase and one for an ethanol/lipid phase) and one outlet well. In practice, a dilution buffer is loaded into the outlet well, this buffer adds backpressure at the output of the device and lowers the ethanol concentration of the final product which stabilizes the particles. Aqueous reagents and lipids in ethanol are loaded into the input wells, a manifold is then clamped oven the inlet wells and pressurized using a syringe or other mechanism. The pressurization pushes the reagents in the inlet wells through the mixer (e.g., a staggered herringbone mixer) and into the outlet well. The formulated particles are then recovered using a pipette. The shown device is designed to have a flow ratio of 3 parts aqueous to 1 part ethanol, which is achieved with different channel lengths leading from the input wells to them mixer. In this case, the ratio of 2.5:1 is used and this takes into account the desired flow ratio and the viscosity difference between the input reagents.

Figure 10:
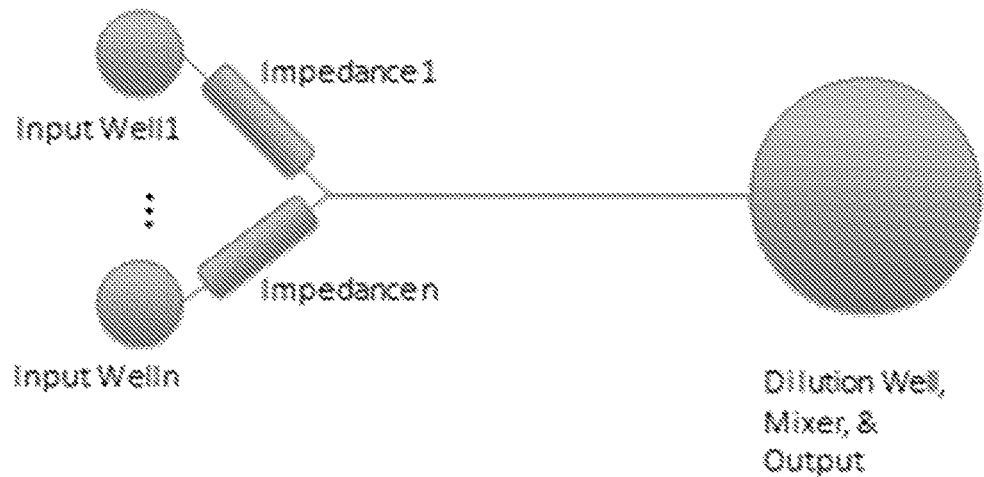

FIG. 10 is a schematic illustration of a representative device and method of the invention for preparing particles at small volumes: a device that flows a first stream of solvent (input wells 1 through n) into a second solvent contained in the outlet reservoir (dilution well). Mixing of the first stream with the contents of the outlet reservoir can occur through various mechanisms including (i) convection flows occurring by introducing the first stream into the reservoir and (ii) active mixing of the combined fluids as the first stream is introduced into the reservoir.

Figure 11:
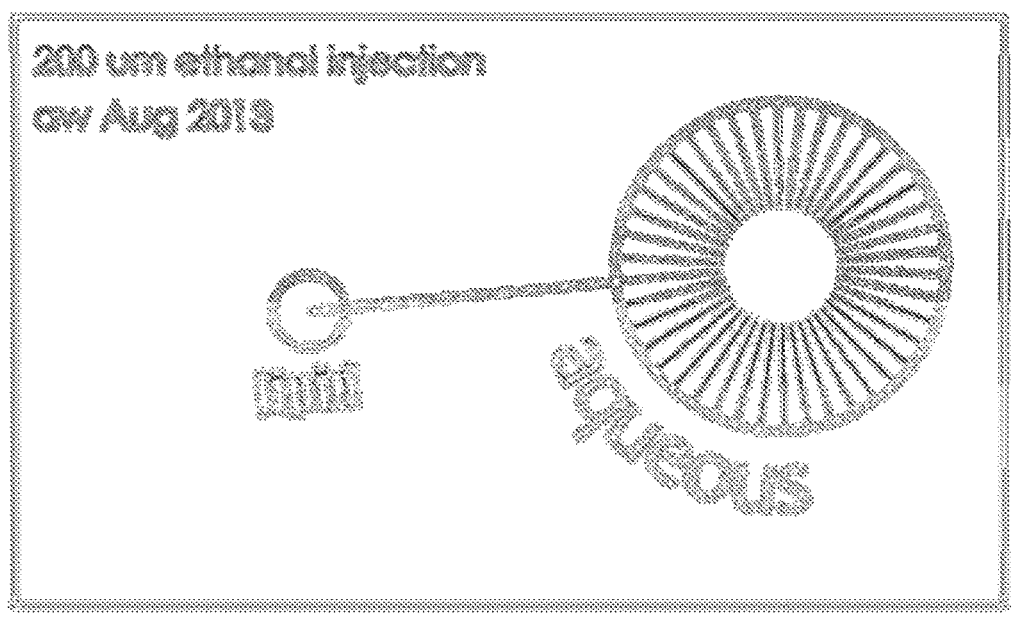

FIG. 11 is an example of a representative device illustrated in the schematic of FIG. 10. The device has a single input well for a lipid/ethanol solution and an outlet well into which an aqueous solution is loaded. The device has a large number of microchannels leading into the outlet well, the impedance of microchannels is high compared to the channel feeding them. This is necessary for an even distribution of fluid. After the reagents are loaded, the inlet well is pressurized. The fluid in the inlet well flows through the microchannels and into the output well. The fluid is mixed by convection and by air bubbles flowing into the outlet well.

Figure 12:
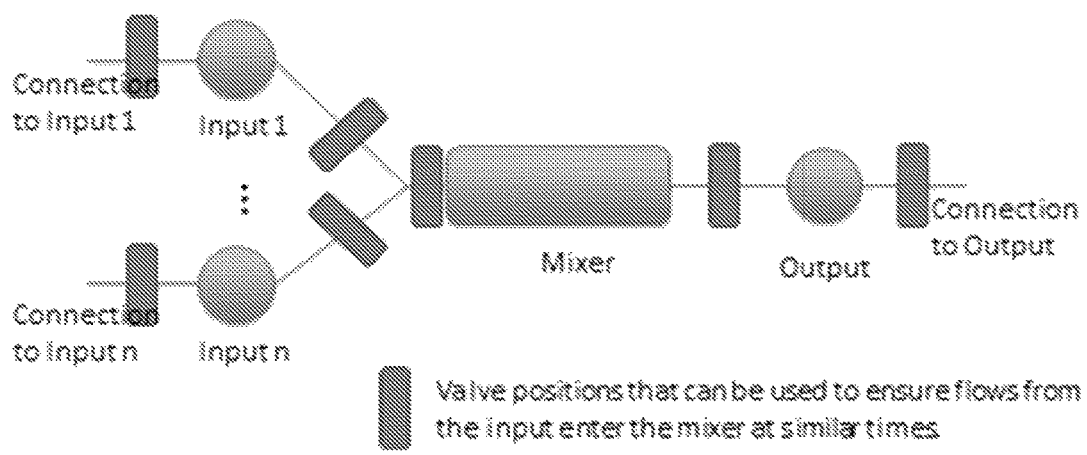

FIG. 12 is a schematic illustration of a representative device and method of the invention for preparing particles at small volumes: a device using valves either at the inlets or outlet to time the introduction of fluidic flows into the mixing chamber.

DETAILED DESCRIPTION OF THE INVENTION

The present invention provides a transfection reagent composition, lipid nanoparticles containing anionic macromolecule(s), methods and devices for making the lipid nanoparticles containing anionic macromolecule(s) using the transfection reagent composition, and methods for transfecting a cell using the lipid nanoparticles.

Transfection Reagent Composition

In one aspect, the invention provides a transfection reagent composition. The transfection reagent composition includes one or more cationic lipids, one or more second lipids, one or more sterols and one or more surfactants.

Lipid Nanoparticles

In one aspect, the invention provides lipid nanoparticles containing anionic macromolecule(s). The lipid nanoparticles include one or more cationic lipids, one or more second lipids, and one or more nucleic acids.

Cationic Lipids

The lipid nanoparticles include a cationic lipid. As used herein, the term "cationic lipid" refers to a lipid that is cationic or becomes cationic (protonated) as the pH is lowered below the pK of the ionizable group of the lipid, but is progressively more neutral at higher pH values. At pH values below the pK, the lipid is then able to associate with negatively charged nucleic acids (e.g., oligonucleotides). As used herein, the term "cationic lipid" includes zwitterionic lipids that assume a positive charge on pH decrease. Cationic lipids useful in the invention do not include PEG-phospholipids (e.g., polyethylene oxide-containing phospholipids).

The term "cationic lipid" refers to any of a number of lipid species which carry a net positive charge at a selective pH, such as physiological pH. Such lipids include, but are not limited to, N,N-dioleyl-N,N-dimethylammonium chloride (DODAC); N-(2,3-dioleyloxy)propyl)-N,N,N-trimethylammonium chloride (DOTMA); N,N-distearyl-N,N-dimethylammonium bromide (DDAB); N-(2,3-dioleyloxy)propyl)-N,N,N-trimethylammonium chloride (DOTAP); 3-(N—(N', N'-dimethylaminoethane)-carbamoyl)cholesterol (DC-Chol); and N-(1,2-dimyristyloxyprop-3-yl)-N,N-dimethyl-N-hydroxyethyl ammonium bromide (DMRIE). Additionally, a number of commercial preparations of cationic lipids are available which can be used in the present invention. These include, for example, LIPOFECTIN® (commercially available cationic liposomes comprising DOTMA and 1,2-dioleoyl-sn-3-phosphoethanolamine (DOPE), from GIBCO/BRL, Grand Island, N.Y.); LIPOFECTAMINE® (commercially available cationic liposomes comprising N-(1-(2,3-dioleyloxy)propyl)-N-(2-(sperminecarboxamido)ethyl)-N,N-dimethyl-ammonium trifluoroacetate (DOSPA) and (DOPE), from GIBCO/BRL); and TRANSFECTAM® (commercially available cationic lipids comprising dioctadecylamidoglycylcarboxyspermine (DOGS) in ethanol from Promega Corp., Madison, Wis.). The following lipids are cationic and have a positive charge at below physiological pH: DODAP, DODMA, DMDMA, 1,2-dilinoleyloxy-N,N-dimethylaminopropane (DLin-DMA), 1,2-dilinolenyloxy-N,N-dimethylaminopropane (DLenDMA), 1,17-bis(2-octylcyclopropyl)heptadecan-9-yl-4-(dimethylamino) butanoate (referred to here as "Cationic Lipid A").

In one embodiment, the cationic lipid is an amino lipid (or a pharmaceutically acceptable salts thereof (e.g., hydrochloride salt)). Suitable amino lipids useful in the invention include those described in WO 2012/016184, incorporated herein by reference in its entirety. Representative amino lipids include 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.C1), 1,2-dilinoleoyl-3-trimethylaminopropane chloride salt (DLin-TAP.C1), 1,2-dilinoleyloxy-3-(N-methylpiperazino) propane (DLin-MPZ), 3-(N,N-dilinoleylamino)-1,2-propanediol (DLinAP), 3-(N,N-dioleylamino)-1,2-propanediou (DOAP), 1,2-dilinoleyloxo-3-(2-N,N-dimethylamino) ethoxypropane (DLin-EG-DMA), and 2,2-dilinoleyl-4-dimethylaminomethyl-[1,3]-dioxolane (DLin-K-DMA), and pharmaceutically acceptable salts thereof (e.g., hydrochloride salts).

Suitable amino lipids include those having the formula:

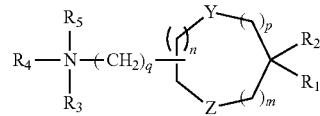

or a pharmaceutically acceptable salt thereof (e.g., hydrochloride salt), wherein $R_1$ and $R_2$ are either the same or different and independently optionally substituted C10-C24 alkyl, optionally substituted C10-C24 alkenyl, optionally substituted C10-C24 alkynyl, or optionally substituted C10-C24 acyl;

$R_3$ and $R_4$ are either the same or different and independently optionally substituted C1-C6 alkyl, optionally substituted C2-C6 alkenyl, or optionally substituted C2-C6 alkynyl or $R_3$ and $R_4$ may join to form an optionally substituted heterocyclic ring of 4 to 6 carbon atoms and 1 or 2 heteroatoms chosen from nitrogen and oxygen;

$R_5$ is either absent or present and when present is hydrogen or C1-C6 alkyl;

m, n, and p are either the same or different and independently either 0 or 1 with the proviso that m, n, and p are not simultaneously 0;

q is 0, 1, 2, 3, or 4; and

Y and Z are either the same or different and independently O, S, or NH.

In another embodiment, the cationic lipid has the formula:

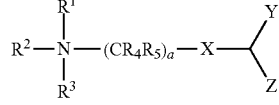

or a pharmaceutically acceptable salt thereof (e.g., hydrochloride), wherein:

$R_1$ and $R_2$ are each independently H, alkyl, alkenyl, alkynyl, cycloalkyl, aryl, heteroaryl, and heterocyclyl, wherein each of alkyl, alkenyl, alkynyl, cycloalkyl, aryl, heteroaryl, and heterocyclyl is optionally substituted by H; halo; hydroxy; cyano; oxo; $C_1$-$C_6$ alkyl optionally substituted by halo, hydroxy, or alkoxy;

or $R_1$ and $R_2$ are taken together with the N atom to which they are both attached to form a 3-8 member heteroaryl or heterocyclyl; wherein each of the heteroaryl and heterocyclyl is optionally substituted by H; halo; hydroxy; cyano; oxo; nitro; $C_1$-$C_6$ alkyl optionally substituted by halo, hydroxyl, or alkoxy;

$R_3$ is absent, H, alkyl, alkenyl, alkynyl, cycloalkyl, aryl, heteroaryl, or heterocyclyl;

$R_4$ and $R_5$ are each independently H, alkyl, alkenyl, alkynyl, cycloalkyl, aryl, heteroaryl, or heterocyclyl;

wherein each of alkyl, alkenyl, alkynyl, cycloalkyl, aryl, heteroaryl, and heterocyclyl is optionally substituted by H; halo; hydroxy; cyano; oxo; $C_1$-$C_6$ alkyl optionally substituted by halo, hydroxy, or alkoxy;

X is —O—, —S—, —$NR_4$—, —S—S—, —OC(=O)—, —C(=O)O—, —OC(=O)O—, —$NR_4$C(=O)—, C(=O)$NR_4$—, —$NR_4$C(=O)O—, —OC(=O)$NR_4$—, —$NR_4$C(=O)$NR_4$—, —$NR_4$C(=S)O—, OC(=S)$NR_4$—, —$NR_4$C(=S)$NR_4$—, —$CR_4R_5$—;

Y and Z are independently $C_{10}$ to $C_{30}$ groups having the formula $L_1$-$(CR_6R_7)_\alpha$—$[L_2$-$(CR_6R_7)_\beta]_\gamma$-$L_3$-$R_8$, wherein $L_1$ is a bond, —$(CR_6R_7)$—, —O—, —CO—, —$NR_8$—, —S—, or a combination thereof;

each $R_6$ and $R_7$, independently, is H; halo; hydroxyl, cyano; $C_1$-$C_6$ alkyl optionally substituted by halo, hydroxyl, or alkoxy:

$L_2$ is a bond, —$(CR_6R_7)$—, —O—, —CO—, —$NR_8$—, —S—,

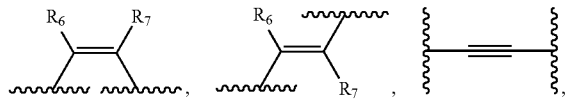

or a combination thereof, or has the formula

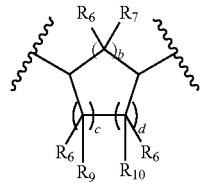

wherein b, c, and d are each independently 0, 1, 2, or 3, given the sum of b, c, and d is at least 1 and no greater than 8; and $R_9$ and $R_{10}$ are each independently $R_7$, or adjacent $R_9$ and $R_{10}$, taken together, are optionally a bond;

$L_3$ is a bond, —$(CR_6R_7)$—, —O—, —CO—, —$NR_8$—, —S—,

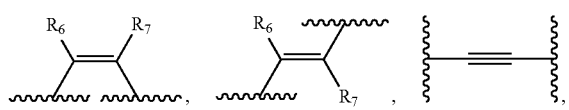

or a combination thereof;

$R_8$ is independently H; halo; hydroxy; cyano; C1-C6 alkyl optionally substituted by halo, hydroxy, or alkoxy; aryl; heteroaryl; or heterocyclyl; or $R_8$ has the formula:

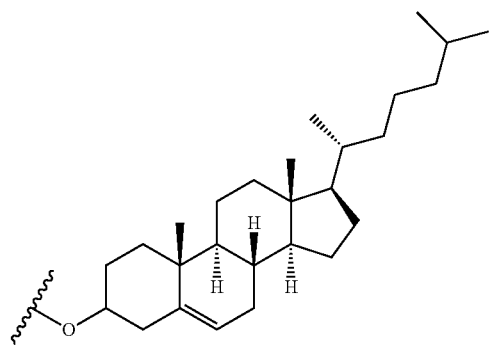

a is 0, 1, 2, 3, or 4;
α is 0-6;
each β, independently, is 0-6;
γ is 0-6.

Other suitable cationic lipids include cationic lipids, which carry a net positive charge at about physiological pH, in addition to those specifically described above, N,N-dioleyl-N,N-dimethylammonium chloride (DODAC); N-(2,3-dioleyloxy)propyl-N,N—N-triethylammonium chloride (DOTMA); N,N-distearyl-N,N-dimethylammonium bromide (DDAB); N-(2,3-dioleoyloxy)propyl)-N,N,N-trimethylammonium chloride (DOTAP); 1,2-dioleyloxy-3-trimethylaminopropane chloride salt (DOTAP.Cl); 3β-(N—(N',N'-dimethylaminoethane)carbamoyl)cholesterol (DC-Chol), N-(1-(2,3-dioleoyloxy)propyl)-N -2-(sperminecarboxamido)ethyl)-N,N-dimethylammoniumtrifluoracetate (DOSPA), dioctadecylamidoglycylcarboxyspermine (DOGS), 1,2-dioleoyl-3-dimethylammonium propane (DODAP), N,N-dimethyl-2,3-dioleoyloxy)propylamine (DODMA), and N-(1,2-dimyristyloxyprop-3-yl)-N,N-dimethyl-N-hydroxyethyl ammonium bromide (DMRIE). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL).

The cationic lipid is present in the transfection reagent composition in an amount from about 30 to about 95 mole percent. In one embodiment, the cationic lipid is present in the transfection reagent composition in an amount from about 30 to about 70 mole percent. In one embodiment, the cationic lipid is present in the transfection reagent composition in an amount from about 40 to about 60 mole percent.

Neutral Lipids

In certain embodiments, the transfection reagent composition includes one or more neutral lipids.

The term "lipid" refers to a group of organic compounds that are esters of fatty acids and are characterized by being insoluble in water but soluble in many organic solvents. Lipids are usually divided in at least three classes: (1) "simple lipids" which include fats and oils as well as waxes; (2) "compound lipids" which include phospholipids and glycolipids; and (3) "derived lipids" such as steroids.

The term "neutral lipid" refers to any one of a number of lipid species that exist in either an uncharged or neutral zwitterionic form at physiological pH. Neutral lipids useful in the invention do not include PEG-phospholipids (e.g. polyethylene oxide-containing phospholipids). Representative neutral lipids include diacylphosphatidylcholines, diacylphosphatidylethanolamines, ceramides, sphingomyelins, dihydrosphingomyelins, cephalins, and cerebrosides.

Exemplary lipids include, for example, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoylphosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearioyl-2-oleoyl-phosphatidyethanol amine (SOPE), and 1,2-dielaidoyl-sn-glycero-3-phophoethanolamine (transDOPE).

In one embodiment, the neutral lipid is 1,2-distearoyl-sn-glycero-3-phosphocholine (DSPC).

Sterols

In certain embodiments, the transfection reagent composition includes one or more sterols.

The term "sterol" refers to a subgroup of steroids also known as steroid alcohols. Sterols are usually divided into two classes: (1) plant sterols also known as "phytosterols"; and (2) animal sterols also known as "zoosterols."

Exemplary sterols include, for example, campesterol, sitosterol, stigmasterol, ergosterol and chloesterol.

In one embodiment, the sterol is cholesterol.

Surfactants

In certain embodiments, the transfection reagent composition includes one or more surfactants.

The term surfactant as used herein, refers to non-ionic, amphipathic compounds that contain both hydrophobic groups and hydrophilic groups. Surfactants useful in the invention do not include PEG-phospholipids (e.g. polyethylene oxide-containing phospholipids).

In one embodiment, a surfactant is represented by the formula

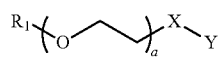

wherein $R_1$ is H, $C_1$-$C_6$ alkyl;

X is —O—, —S—, —NR$_2$—, —S—S—, —OC(=O)—, —C(=O)O—, —OC(=O)O—, —NR$_2$C(=O)—, C(=O)NR$_2$—, —NR$_2$C(=O)O—, —OC(=O)NR$_2$—, —NR$_2$C(=O)NR$_2$—, —NR$_2$C(=S)O—, OC(=S)NR$_2$—, —NR$_2$C(=S)NR$_2$—, —CR$_2$R$_3$—;

R$_2$ and R$_3$ are each independently H, alkyl, alkenyl, alkynyl, cycloalkyl, aryl, heteroaryl, or heterocyclyl;

wherein each of alkyl, alkenyl, alkynyl, cycloalkyl, aryl, heteroaryl, and heterocyclyl is optionally substituted by H; halo; hydroxy; cyano; oxo; $C_1$-$C_6$ alkyl optionally substituted by halo, hydroxy, or alkoxy;

Y is a $C_{10}$ to $C_{40}$ group having the formula L$_1$-(CR$_4$R$_5$)$_\alpha$-[L$_2$-(CR$_4$R$_5$)$_\beta$]$_\gamma$-L$_3$-R$_6$, wherein:

L$_1$ is a bond, —(CR$_4$R$_5$)—, —O—, —CO—, —NR$_2$—, —S—, or a combination thereof; each R$_4$ and R$_5$, independently, is H; halo; hydroxyl; cyano; $C_1$-$C_6$ alkyl optionally substituted by halo, hydroxyl, or alkoxy;

L$_2$ and L$_3$ each, independently, are a bond, —(CR$_4$R$_5$)—, —O—, —CO—, —NR$_2$—, —S—,

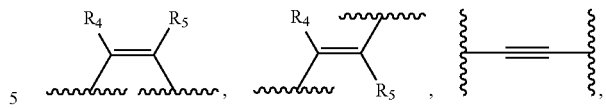

or a combination thereof;

R$_6$ is independently H; halo; hydroxy; cyano; $C_1$-$C_6$ alkyl optionally substituted by halo, hydroxy, or alkoxy; aryl; heteroaryl; or heterocyclyl; or R$_6$ has the formula:

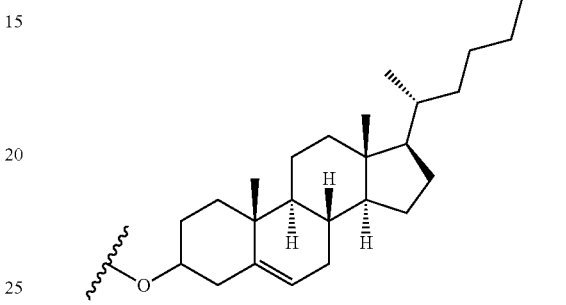

a is 2-100;

α is 0-6;

each β, independently, is 0-6;

γ is 0-6.

In another embodiment, a surfactant is represented by the formula

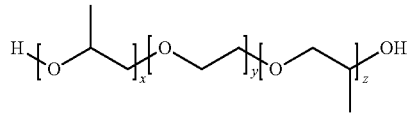

wherein:

x=1 to 50;

y=1 to 50; and z=1 to 50.

In another embodiment, a surfactant is represented by the formula

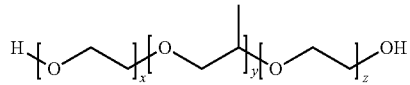

wherein:

x=1 to 50;

y=1 to 50; and z=1 to 50.

In certain embodiments, the surfactant is selected from the group consisting of polyoxyethylene alkyl ethers, polyoxyethylene alkyl esters, diblock polyoxyethylene alkyl ether co-polymers and triblock polyoxyethylene alkyl ether co-polymers. Suitable surfactants include polyoxyethylene (20) oleyl ether, polyoxyethylene (23) lauryl ether, polyoxyethylene (40) stearate, poly(propylene glycol)$_{11}$-block-poly(ethylene glycol)$_{16}$-block-poly(propylene glycol)$_{11}$, poly(propylene glycol)$_{12}$-block-poly(ethylene glycol)$_{28}$-block-poly(propylene glycol)$_{12}$ In certain embodiments, the surfactant is present in the transfection reagent composition in an amount from about 0.1 to about 20 mole percent. In one embodiment, the surfactant is present in the transfection reagent composition in an amount from about 0.5 to about 10 mole percent. In one embodiment, the surfactant is present in the lipid nanoparticle in about 2 mole percent.

In one embodiment, the surfactant is polyoxyethylene (20) oleyl ether.

In one embodiment, the surfactant is polyoxyethylene (40) stearate.

In one embodiment, the transfection reagent composition includes:

(a) a cationic lipid that is an aminolipid or a pharmaceutically acceptable salt thereof;

(b) a neutral lipid that is a phospholipid;

(c) a sterol that is cholesterol; and (d) a surfactant that is selected from polyoxyethylene (20) oleyl ether, polyoxyethylene (23) lauryl ether, or polyoxyethylene (40) stearate.

In another embodiment, the transfection reagent composition includes:

(a) a cationic lipid that is 1,17-bis(2-octylcyclopropyl) heptadecan-9-yl-4-(dimethylamino)butanoate or a pharmaceutically acceptable salt thereof;

(b) a neutral lipid that is 1,2-distearoyl-sn-glycero-3-phosphocholine (DSPC);

(c) a sterol that is cholesterol; and (d) a surfactant that is selected from polyoxyethylene (20) oleyl ether, polyoxyethylene (23) lauryl ether, or polyoxyethylene (40) stearate.

In certain embodiments, the transfection reagent compositions of the invention do not include PEG-phospholipids (e.g. polyethylene oxide-containing phospholipids).

Anionic Macromolecules

The lipid nanoparticles of the present invention are useful for the systemic or local delivery of anionic macromolecules. As described herein, the transfection reagent composition is mixed with the anionic macromolecule which is incorporated into the resulting lipid nanoparticle.

As used herein, the term "anionic macromolecule" refers to a macromolecule that is anionic or becomes anionic (deprotonated) as the pH is increased above the pK of the ionizable group of the macromolecule, but is progressively more neutral at lower pH values. At pH values above the pK, the macromolecule is then able to associate with positively charged lipids (e.g., cationic lipids). As used herein, the term "anionic macromolecule" includes zwitterionic macromolecules that assume a negative charge on pH increase.

The term "anionic macromolecule" refers to any of a number of species which carry a net negative charge at a selective pH, such as physiological pH. Such macromolecules include, but are not limited to, nucleic acids, proteins, peptides and carbohydrates.

Nucleic Acids

The lipid nanoparticles of the present invention are useful for the systemic or local delivery of nucleic acids. As described herein, the transfection reagent composition is mixed with the nucleic acid which is incorporated into the resulting lipid nanoparticle.

As used herein, the term "nucleic acid" is meant to include any oligonucleotide or polynucleotide. Fragments containing up to 50 nucleotides are generally termed oligonucleotides, and longer fragments are called polynucleotides. In particular embodiments, oligonucleotides of the present invention are 20-50 nucleotides in length. In the context of this invention, the terms "polynucleotide" and "oligonucleotide" refer to a polymer or oligomer of nucleotide or nucleoside monomers consisting of naturally occurring bases, sugars and intersugar (backbone) linkages. The terms "polynucleotide" and "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases. Oligonucleotides are classified as deoxyribooligonucleotides or ribooligonucleotides. A deoxyribooligonucleotide consists of a 5-carbon sugar called deoxyribose joined covalently to phosphate at the 5' and 3' carbons of this sugar to form an alternating, unbranched polymer. A ribooligonucleotide consists of a similar repeating structure where the 5-carbon sugar is ribose. The nucleic acid that is present in a lipid nanoparticle according to this invention includes any form of nucleic acid that is known. The nucleic acids used herein can be single-stranded DNA or RNA, or double-stranded DNA or RNA, or DNA-RNA hybrids. Examples of double-stranded DNA include structural genes, genes including control and termination regions, and self-replicating systems such as viral or plasmid DNA. Examples of double-stranded RNA include siRNA and other RNA interference reagents. Single-stranded nucleic acids include antisense oligonucleotides, ribozymes, microRNA, and triplex-forming oligonucleotides.

In one embodiment, the polynucleic acid is an antisense oligonucleotide. In certain embodiments, the nucleic acid is an antisense nucleic acid, a ribozyme, tRNA, snRNA, siRNA, shRNA, ncRNA, miRNA, pre-condensed DNA, or an aptamer.

The term "nucleic acids" also refers to ribonucleotides, deoxynucleotides, modified ribonucleotides, modified deoxyribonucleotides, modified phosphate-sugar-backbone oligonucleotides, other nucleotides, nucleotide analogs, and combinations thereof, and can be single stranded, double stranded, or contain portions of both double stranded and single stranded sequence, as appropriate.

The term "nucleotide," as used herein, generically encompasses the following terms, which are defined below: nucleotide base, nucleoside, nucleotide analog, and universal nucleotide.

The term "nucleotide base," as used herein, refers to a substituted or unsubstituted parent aromatic ring or rings. In some embodiments, the aromatic ring or rings contain at least one nitrogen atom. In some embodiments, the nucleotide base is capable of forming Watson-Crick and/or Hoogsteen hydrogen bonds with an appropriately complementary nucleotide base. Exemplary nucleotide bases and analogs thereof include, but are not limited to, purines such as 2-aminopurine, 2,6-diaminopurine, adenine (A), ethenoadenine, N6-2-isopentenyladenine (6iA), N6-2-isopentenyl-2-methylthioadenine (2 ms6iA), N6-methyladenine, guanine (G), isoguanine, N2-dimethylguanine (dmG), 7-methylguanine (7 mG), 2-thiopyrimidine, 6-thioguanine (6sG) hypoxanthine and O6-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, O4-methylthymine, uracil (U), 4-thiouracil (4sU) and 5,6-dihydrouracil (dihydrouracil; D); indoles such as nitroindole and 4-methylindole; pyrroles such as nitropyrrole; nebularine; base (Y); in some embodiments, nucleotide bases are universal nucleotide bases. Additional exemplary nucleotide bases can be found in Fasman, 1989, *Practical*

*Handbook of Biochemistry and Molecular Biology*, pp. 385-394, CRC Press, Boca Raton, Fla., and the references cited therein. Further examples of universal bases can be found, for example, in Loakes, N. A. R. 2001, 29:2437-2447, and Seela N. A. R. 2000, 28:3224-3232.

The term "nucleoside," as used herein, refers to a compound having a nucleotide base covalently linked to the C-1' carbon of a pentose sugar. In some embodiments, the linkage is via a heteroaromatic ring nitrogen. Typical pentose sugars include, but are not limited to, those pentoses in which one or more of the carbon atoms are each independently substituted with one or more of the same or different —R, —OR, —NRR or halogen groups, where each R is independently hydrogen, (C1-C6) alkyl or (C5-C14) aryl. The pentose sugar may be saturated or unsaturated. Exemplary pentose sugars and analogs thereof include, but are not limited to, ribose, 2'-deoxyribose, 2'-(C1-C6)alkoxyribose, 2'-(C5-C14)aryloxyribose, 2',3'-dideoxyribose, 2',3'-didehydrori-bose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose. Also see, e.g., 2'-O-methyl, 4'-α-anomeric nucleotides, 1'-α-anomeric nucleotides (Asseline (1991) *Nucl. Acids Res.* 19:4067-74), 2'-4'- and 3'-4'-linked and other "locked" or "LNA," bicyclic sugar modifications (WO 98/22489; WO 98/39352; WO 99/14226). "LNA" or "locked nucleic acid" is a DNA analogue that is conformationally locked such that the ribose ring is constrained by a methylene linkage between the 2'-oxygen and the 3'- or 4'-carbon. The conformation restriction imposed by the linkage often increases binding affinity for complementary sequences and increases the thermal stability of such duplexes.

Sugars include modifications at the 2'- or 3'-position such as methoxy, ethoxy, allyloxy, isopropoxy, butoxy, isobutoxy, methoxyethyl, alkoxy, phenoxy, azido, amino, alkylamino, fluoro, chloro and bromo. Nucleosides and nucleotides include the natural D configurational isomer (D-form), as well as the L configurational isomer (L-form) (Beigelman, U.S. Pat. No. 6,251,666; Chu, U.S. Pat. No. 5,753,789; Shudo, EP0540742; Garbesi (1993) *Nucl. Acids Res.* 21:4159-65; Fujimori (1990) *J. Amer. Chem. Soc.* 112:7435; Urata, (1993) *Nucleic Acids Symposium Ser. No.* 29:69-70). When the nucleobase is purine, e.g., A or G, the ribose sugar is attached to the N9-position of the nucleobase. When the nucleobase is pyrimidine, e.g., C, T or U, the pentose sugar is attached to the N1-position of the nucleobase (Kornberg and Baker, (1992) *DNA Replication*, 2 nd Ed., Freeman, San Francisco, Calif.).

One or more of the pentose carbons of a nucleoside may be substituted with a phosphate ester. In some embodiments, the phosphate ester is attached to the 3'- or 5'-carbon of the pentose. In some embodiments, the nucleosides are those in which the nucleotide base is a purine, a 7-deazapurine, a pyrimidine, a universal nucleotide base, a specific nucleotide base, or an analog thereof.

The term "nucleotide analog," as used herein, refers to embodiments in which the pentose sugar and/or the nucleotide base and/or one or more of the phosphate esters of a nucleoside may be replaced with its respective analog. In some embodiments, exemplary pentose sugar analogs are those described above. In some embodiments, the nucleotide analogs have a nucleotide base analog as described above. In some embodiments, exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, and may include associated counterions. Other nucleic acid analogs and bases include for example intercalating nucleic acids (INAs, as described in Christensen and Pedersen, 2002), and AEGIS bases (Eragen, U.S. Pat. No. 5,432,272). Additional descriptions of various nucleic acid analogs can also be found for example in (Beaucage et al., *Tetrahedron* 49(10):1925 (1993) and references therein; Letsinger, *J. Org. Chem.* 35:3800 (1970); Sprinzl et al., *Eur. J. Biochem.* 81:579 (1977); Letsinger et al., *Nucl. Acids Res.* 14:3487 (1986); Sawai et al., *Chem. Lett.* 805 (1984), Letsinger et al., *J. Am. Chem. Soc.* 110:4470 (1988); and Pauwels et al., *ChemicaScripta* 26:141 (1986)), phosphorothioate (Mag et al., *Nucleic Acids Res.* 19:1437 (1991); and U.S. Pat. No. 5,644,048. Other nucleic analogs comprise phosphorodithioates (Briu et al., *J. Am. Chem. Soc.* 111:2321 (1989)), O-methylphosphoroamidite linkages (see Eckstein, *Oligonucleotides and Analogues: A Practical Approach*, Oxford University Press), those with positive backbones (Denpcy et al., *Proc. Natl. Acad. Sci. USA* 92:6097 (1995); non-ionic backbones (U.S. Pat. Nos. 5,386,023; 5,386,023; 5,637,684; 5,602,240; 5,216,141; and 4,469,863; Kiedrowski et al., *Angew. Chem. Intl. Ed. English* 30:423 (1991); Letsinger et al., *J. Am. Chem. Soc.* 110:4470 (1988); Letsinger et al., *Nucleoside & Nucleotide* 13:1597 (194): Chapters 2 and 3, *ASC Symposium Series* 580, "Carbohydrate Modifications in Antisense Research," Ed. Y. S. Sanghui and P. Dan Cook; Mesmaeker et al., *Bioorganic & Medicinal Chem. Lett.* 4:395 (1994); Jeffs et al., *J. Biomolecular NMR* 34:17 (1994); *Tetrahedron Lett.* 37:743 (1996)) and non-ribose backbones, including those described in U.S. Pat. Nos. 5,235,033 and 5,034,506, and Chapters 6 and 7, *ASC Symposium Series* 580, "Carbohydrate Modifications in Antisense Research," Ed. Y. S. Sanghui and P. Dan Cook. Nucleic acids containing one or more carbocyclic sugars are also included within the definition of nucleic acids (see Jenkins et al., *Chem. Soc. Rev.* (1995), pp. 169-176). Several nucleic acid analogs are also described in Rawls, *C & E News*, Jun. 2, 1997, page 35.

The term "universal nucleotide base" or "universal base," as used herein, refers to an aromatic ring moiety, which may or may not contain nitrogen atoms. In some embodiments, a universal base may be covalently attached to the C-1' carbon of a pentose sugar to make a universal nucleotide. In some embodiments, a universal nucleotide base does not hydrogen bond specifically with another nucleotide base. In some embodiments, a universal nucleotide base hydrogen bonds with nucleotide base, up to and including all nucleotide bases in a particular target polynucleotide. In some embodiments, a nucleotide base may interact with adjacent nucleotide bases on the same nucleic acid strand by hydrophobic stacking Universal nucleotides include, but are not limited to, deoxy-7-azaindole triphosphate (d7AITP), deoxyisocarbostyril triphosphate (dICSTP), deoxypropynylisocarbostyril triphosphate (dPICSTP), deoxymethyl-7-azaindole triphosphate (dM7AITP), deoxyImPy triphosphate (dImPyTP), deoxyPP triphosphate (dPPTP), or deoxypropynyl-7-azaindole triphosphate (dP7AITP). Further examples of such universal bases can be found, inter alia, in Published U.S. application Ser. No. 10/290,672, and U.S. Pat. No. 6,433,134.

As used herein, the terms "polynucleotide" and "oligonucleotide" are used interchangeably and mean single-stranded and double-stranded polymers of nucleotide monomers, including 2'-deoxyribonucleotides (DNA) and ribonucleotides (RNA) linked by internucleotidephosphodiester bond linkages, e.g., 3'-5' and 2'-5', inverted linkages, e.g., 3'-3' and 5'-5', branched structures, or internucleotide analogs. Polynucleotides have associated counter ions, such as H+, NH4+, trialkylammonium, Mg2+, Na+, and the like. A polynucleotide may be composed entirely of deoxyribonucleotides, entirely of ribonucleotides, or chimeric compositions thereof. Polynucleotides may be comprised of internucleotide, nucleobase and/or sugar analogs. Polynucleotides typically range in size from a few monomeric units, e.g., 3-40 when they are more commonly frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytosine, "G" denotes deoxyguanosine, and "T" denotes thymidine, unless otherwise noted.

Figure 2:
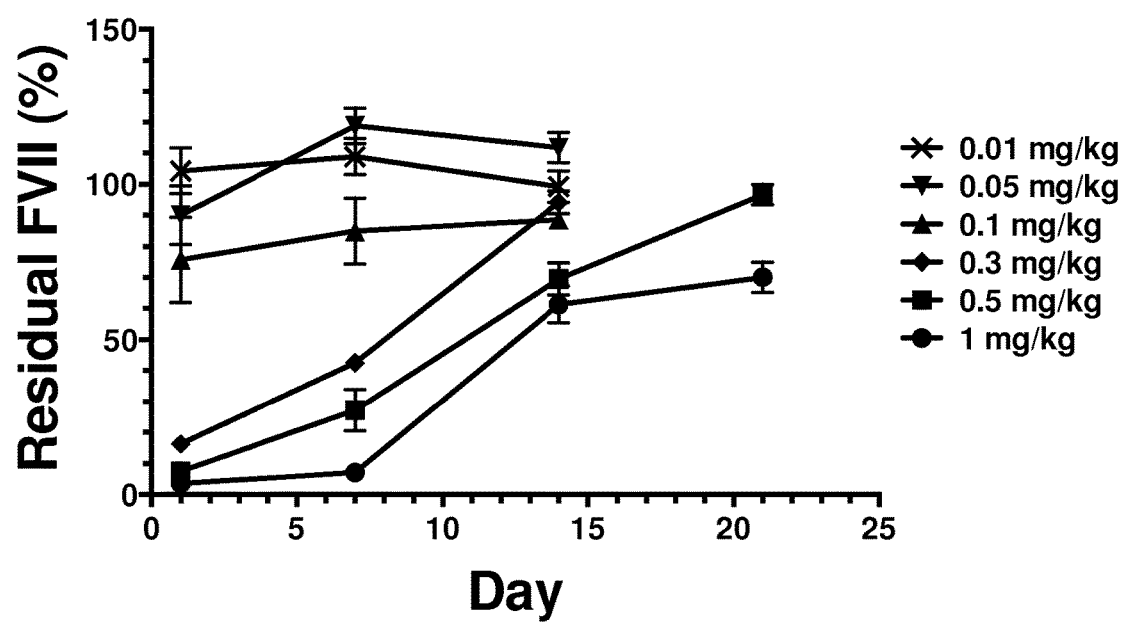
FIG. 2 uses the Factor VII (FVII) Mouse Model to illustrate the in vivo silencing activity of siRNA-LNP prepared with the surfactant polyoxyethylene (40) stearate.

As used herein, "nucleobase" means those naturally occurring and those non-naturally occurring heterocyclic moieties commonly known to those who utilize nucleic acid technology or utilize peptide nucleic acid technology to thereby generate polymers that can sequence specifically bind to nucleic acids. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). Other non-limiting examples of suitable nucleobase include those nucleobases illustrated in FIGS. 2(A) and 2(B) of Buchardt et al. (WO92/20702 or WO92/20703).

As used herein, "nucleobase sequence" means any segment, or aggregate of two or more segments (e.g., the aggregate nucleobase sequence of two or more oligomer blocks), of a polymer that comprises nucleobase-containing subunits. Non-limiting examples of suitable polymers or polymers segments include oligodeoxynucleotides (e.g., DNA), oligoribonucleotides (e.g., RNA), peptide nucleic acids (PNA), PNA chimeras, PNA combination oligomers, nucleic acid analogs and/or nucleic acid mimics.

As used herein, "polynucleobase strand" means a complete single polymer strand comprising nucleobase subunits. For example, a single nucleic acid strand of a double stranded nucleic acid is a polynucleobase strand.

As used herein, "nucleic acid" is a nucleobase sequence-containing polymer, or polymer segment, having a backbone formed from nucleotides, or analogs thereof.

Preferred nucleic acids are DNA and RNA.

As used herein, nucleic acids may also refer to "peptide nucleic acid" or "PNA" means any oligomer or polymer segment (e.g., block oligomer) comprising two or more PNA subunits (residues), but not nucleic acid subunits (or analogs thereof), including, but not limited to, any of the oligomer or polymer segments referred to or claimed as peptide nucleic acids in U.S. Pat. Nos. 5,539,082; 5,527,675; 5,623,049; 5,714,331; 5,718,262; 5,736,336; 5,773,571; 5,766,855; 5,786,461; 5,837,459; 5,891,625; 5,972,610; 5,986,053; and 6,107,470; each of which is herein incorporated by reference. The term "peptide nucleic acid" or "PNA" shall also apply to any oligomer or polymer segment comprising two or more subunits of those nucleic acid mimics described in the following publications: Lagriffoul et al., Bioorganic & Medicinal Chemistry Letters, 4:1081-1082 (1994); Petersen et al., *Bioorganic & Medicinal Chemistry Letters* 6:793-796 (1996); Diderichsen et al., *Tett. Lett.* 37:475-478 (1996); Fujii et al., *Bioorg. Med. Chem. Lett.* 7:637-627 (1997); Jordan et al., *Bioorg. Med. Chem. Lett.* 7:687-690 (1997); Krotz et al., *Tett. Lett.* 36:6941-6944 (1995); Lagriffoul et al., *Bioorg. Med. Chem. Lett.* 4:1081-1082 (1994); Diederichsen, U., *Bioorganic & Medicinal Chemistry Letters* 7:1743-1746 (1997); Lowe et al., *J. Chem. Soc. Perkin Trans.* 1, (1997) 1:539-546; Lowe et al., *J. Chem. Soc. Perkin Trans.* 11:547-554 (1997); Lowe et al., *J. Chem. Soc. Perkin Trans.* 11:555-560 (1997); Howarth et al., *J. Org. Chem.* 62:5441-5450 (1997); Altmann, K.-H., et al., *Bioorganic & Medicinal Chemistry Letters* 7:1119-1122 (1997); Diederichsen, U., *Bioorganic & Med. Chem. Lett.* 8:165-168 (1998); Diederichsen et al., *Angew. Chem. Int. Ed.* 37:302-305 (1998); Cantin et al., *Tett. Lett.* 38:4211-4214 (1997); Ciapetti et al., *Tetrahedron* 53:1167-1176 (1997); Lagriffoule et al., *Chem. Eur. J.* 3:912-919 (1997); Kumar et al., *Organic Letters* 3(9):1269-1272 (2001); and the Peptide-Based Nucleic Acid Mimics (PENAMS) of Shah et al. as disclosed in WO96/04000.

The lipid nanoparticle of the invention differs from other similarly constituted materials by its morphology and characterized as having a substantially solid core. A lipid nanoparticle having a substantially solid core is a particle that does not have extended aqueous regions on the interior and that has an interior that is primarily lipid. In one embodiment, an extended region is a continuous aqueous region with a volume greater than half the particle volume. In a second embodiment, an extended aqueous region is more than 25% of the particle volume. The extent of internal aqueous regions may be determined by electron microscopy and appear as regions of low electron density. Further, because the interior of the solid core nanoparticle is primarily lipid, the aqueous content of the particle (the "trapped volume") per lipid constituting the particle is less than that expected for a unilamellar bilayer lipid vesicle with the same radius. In one embodiment, the trapped volume is less than 50% of that expected for a unilamellar bilayer vesicle with the same radius. In a second embodiment, the trapped volume is less than 25% of that expected for a unilamellar bilayer vesicle of the same size. In a third embodiment, the trapped volume is less than 20% of the total volume of the particle. In one embodiment, the trapped volume per lipid is less than 2 microliter per micromole lipid. In another embodiment the trapped volume is less than 1 microliter per micromole lipid. In addition, while the trapped volume per lipid increases substantially for a bilayer lipid vesicle as the radius of the vesicle is increased, the trapped volume per lipid does not increase substantially as the radius of solid core nanoparticles is increased. In one embodiment, the trapped volume per lipid increases by less than 50% as the mean size is increased from a diameter of 20 nm to a diameter of 100 nm. In a second embodiment, the trapped volume per lipid increases by less than 25% as the mean size is increased from a diameter of 20 nm to a diameter of 100 nm. The trapped volume can be measured employing a variety of techniques described in the literature. Because solid core systems contain lipid inside the particle, the total number of particles of a given radius generated per mole of lipid is less than expected for bilayer vesicle systems. The number of particles generated per mol of lipid can be measured by fluorescence techniques amongst others.

The lipid nanoparticles of the invention can also be characterized by electron microscopy. The particles of the invention having a substantially solid core have an electron dense core as seen by electron microscopy. Electron dense is defined such that area-averaged electron density of the interior 50% of the projected area of a solid core particle (as seen in a 2-D cryo EM image) is not less than x % (x=20%, 40%, 60%) of the maximum electron density at the periphery of the particle. Electron density is calculated as the absolute value of the difference in image intensity of the region of interest from the background intensity in a region containing no nanoparticle.

Encapsulation Efficiency

The lipid nanoparticles of the invention can be further distinguished by the encapsulation efficiency. As described below, the lipid nanoparticles of the invention are prepared by a process by which nearly 100% (e.g., 80-100%) of the nucleic acid used in the formation process is encapsulated in the particles. In one embodiment, the lipid nanoparticles are prepared by a process by which from about 90 to about 95% of the nucleic acid used in the formation process is encapsulated in the particles.

Microfluidic Methods for Making Lipid Nanoparticles

In one aspect, the invention provides a method for making lipid nanoparticles containing an anionicmacromolecule using the lipid transfection reagent composition. In one embodiment, the method includes:

(a) introducing a first stream comprising an anionic macromolecules (e.g., polynucleic acid) in a first solvent into a microchannel; wherein the microchannel has a first region adapted for flowing one or more streams introduced into the microchannel and a second region for mixing the contents of the one or more streams;

(b) introducing a second stream comprising transfection reagent composition in a second solvent in the microchannel to provide first and second streams flowing in the device, wherein the transfection reagent composition comprises an ionizable cationic lipid, a neutral lipid, a sterol and a surfactant and wherein the first and second solvents are not the same;

(c) flowing the one or more first streams and the one or more second streams from the first region of the microchannel into the second region of the microchannel; and (d) mixing of the contents of the one or more first streams and the one or more second streams flowing in the second region of the microchannel to provide a third stream comprising lipid nanoparticles with encapsulated anionic macromolecules.

The contents of the first and second streams can be mixed by chaotic advection. In one embodiment, mixing the contents of the one or more first streams and the one or more second streams comprises varying the concentration or relative mixing rates of the one or more first streams and the one or more second streams. In the above embodiment, unlike known methods, the method does not include a dilution after mixing.

To further stabilize the third stream containing the lipid nanoparticles with encapsulated anionic macromolecules, the method can, but need not further include, comprising diluting the third stream with an aqueous buffer. In one embodiment, diluting the third stream includes flowing the third stream and an aqueous buffer into a second mixing structure. In another embodiment, the aqueous buffer comprising lipid nanoparticles with encapsulated anionic macromolecules is dialyzed to reduce the amount of the second solvent.

The first stream includes anionic macromolecules in a first solvent. Suitable first solvents include solvents in which the anionic macromolecules are soluble and that are miscible with the second solvent. Suitable first solvents include aqueous buffers. Representative first solvents include citrate and acetate buffers.

The second stream includes transfection reagent composition in a second solvent. Suitable second solvents include solvents in which the lipids and surfactants are soluble and that are miscible with the first solvent. Suitable second solvents include 1,4-dioxane, tetrahydrofuran, acetone, acetonitrile, dimethyl sulfoxide, dimethylformamide, acids, and alcohols. Representative second solvents include aqueous ethanol 90%.

The methods of the invention are distinguished from other microfluidic mixing methods in several ways. Whereas certain known methods require an equal or substantially equal proportion of aqueous and organic solvents (i.e., 1:1), the method of the invention generally utilizes a solvent ratio of aqueous to organic that exceeds 1:1. In certain embodiments, the solvent ratio of aqueous to organic is about 2:1. In certain embodiments, the solvent ratio of aqueous to organic is about 3:1. In certain embodiments, the solvent ratio of aqueous to organic is about 4:1. In certain other embodiments, the solvent ratio of aqueous to organic is about 5:1, about 10:1, about 50:1, about 100:1, or greater.

The lipid nanoparticles of the invention are advantageously formed in a microfluidic process that utilizes relatively rapid mixing and high flow rates. The rapid mixing provides lipid nanoparticles having the advantageous properties noted above including size, homogeneity, encapsulation efficiency. Mixing rates used in the practice of the method of the invention range from about 100 μsec to about 10 msec. Representative mixing rates include from about 1 to about 5 msec. Whereas hydrodynamic flow focusing methods operate at relatively low flow rates (e.g., 5 to 100 μL/minute) with relatively low lipid volumes, the method of the invention operates at relatively high flow rates and relatively high lipid volumes. In certain embodiments, for methods that incorporate a single mixing region (i.e., mixer), the flow rate is about 10 mL/min. For methods of the invention that utilize mixer arrays (e.g., 10 mixers), flow rates of 100 mL/minute are employed (for 100 mixers, flow rate 1000 mL/min). Thus, the methods of the invention can be readily scaled to provide quantities of lipid nanoparticles necessary for demanding production requirements. Coupled with the advantageous particle size and homogeneity and encapsulation efficiencies realized, the method of the invention overcomes disadvantages of known microfluidic methods for producing the lipid nanoparticles. One advantage of the methods of the invention for making the lipid nanoparticles is that the methods are scalable, which means that the methods do not change on scaling and that there is excellent correspondence on scaling.

Microfluidic Devices for Making Lipid Nanoparticles

In another aspect, the invention provides devices for producing a lipid nanoparticle encapsulating an anionic macromolecule using the transfection reagent composition. In one embodiment the device includes:

(a) a first inlet for receiving a first solution comprising a nucleic acid in a first solvent;

(b) a first inlet microchannel in fluid communication with the first inlet to provide a first stream comprising the nucleic acid in the first solvent;

(c) a second inlet for receiving a second solution comprising transfection reagent composition in a second solvent;

(d) a second inlet microchannel in fluid communication with the second inlet to provide a second stream comprising the transfection reagent composition in the second solvent; and (e) a third microchannel for receiving the first and second streams, wherein the third microchannel has a first region adapted for flowing the first and second streams introduced into the microchannel and a second region adapted for mixing the contents of the first and second streams to provide a third stream comprising lipid nanoparticles with encapsulated nucleic acid.

In one embodiment, the device further includes means for diluting the third stream to provide a diluted stream comprising stabilized lipid nanoparticles with encapsulated anionic macromolecules.

The device of the invention is a microfluidic device including one or more microchannels (i.e., a channel having its greatest dimension less than 1 millimeter). In one embodiment, the microchannel has a hydrodynamic diameter from about 20 to about 300 μm. As noted above, the microchannel has two regions: a first region for receiving and flowing at least two streams (e.g., one or more first streams and one or more second streams) into the device. The contents of the first and second streams are mixed in the microchannel's second region. In one embodiment, the second region of the microchannel has a principal flow direction and one or more surfaces having at least one groove or protrusion defined therein, the groove or protrusion having an orientation that forms an angle with the principal direction (e.g., a staggered herringbone mixer), as described in U.S. Application Publication No. 2004/0262223, expressly incorporated herein by reference in its entirety. In one embodiment, the second region of the microchannel comprises bas-relief structures. To achieve maximal mixing rates, it is advantageous to avoid undue fluidic resistance prior to the mixing region. Thus, one embodiment of the invention is a device in which non-microfluidic channels, having dimensions greater than 1000 microns, are used to deliver the fluids to a single mixing channel.

In one embodiment the microfluidic device was produced by soft lithography, the replica molding of microfabricated masters in elastomer. The device has two inlets, one for each of the solutions prepared above, and one outlet. The microfluidic device was produced by soft lithography, the replica molding of microfabricated masters in elastomer. The device features a 300 μm wide and approximately 130 μm high mixing channel with herringbone structures formed by approximately 40 μm high and 75 m thick features on the roof of the channel. The device was sealed using an oxygen plasma treatment to a 40×36×2 mm glass slide with three 1.5 mm holes drilled to match the inlet and outlet ports of the device.

In a second embodiment, microfluidic devices are produced from a hard thermoplastic such as cyclic olefin copolymer. A negative tool was machined using a CNC mill and devices formed using injection molding. Channel dimensions were preserved with the addition of a draft angle ranging between 1° and 5° on vertical surfaces. Molded pieces were sealed to a blank substrate using a variety of techniques, including but not limited to: lamination, solvent welding, heat pressing and combinations thereof. Bonded devices were annealed to remove residual stresses from the production processes. Once formed, devices were installed and used in the custom instrument in the same way as elastomer devices.

In other aspects of the invention, the first and second streams are mixed with other micromixers. Suitable micromixers include droplet mixers, T-mixers, zigzag mixers, multilaminate mixers, or other active mixers.

Mixing of the first and second streams can also be accomplished with means for varying the concentration and relative flow rates of the first and second streams.

In another embodiment, the device for producing a lipid nanoparticle encapsulating a anionic macromolecule includes microchannel for receiving the first and second streams, wherein the microchannel has a first region adapted for flowing the first and second streams introduced into the microchannel and a second region adapted for mixing the contents of the first and second streams to provide a third stream comprising lipid nanoparticles with encapsulated anionic macromolecules. In this embodiment, the first and second streams are introduced into the microchannel by means other than first and second microchannels as noted above.

To achieve maximal mixing rates it is advantageous to avoid undue fluidic resistance prior to the mixing region. Thus one embodiment of the invention is a device in which non-microfluidic channels, having dimensions greater than 1000 microns, are used to deliver fluids to a single mixing channel. This device for producing a lipid nanoparticle encapsulating an anionic macromolecule includes:

(a) a single inlet microchannel for receiving both a first solution comprising an anionic macromolecule in a first solvent and a second solution comprising transfection reagent composition in a second solvent; and (b) a second region adapted for mixing the contents of the first and second streams to provide a third stream comprising lipid nanoparticles with encapsulated anionic macromolecule.

In such an embodiment, the first and second streams are introduced into the microchannel by a single inlet or by one or two channels not having micro-dimensions, for example, a channel or channels having dimensions greater than 1000 μm (e.g., 1500 or 2000 μm or larger). These channels may be introduced to the inlet microchannel using adjacent or concentric macrosized channels.

Method for Delivering Anionic Macromolecules Using Lipid Nanoparticles

The transfection reagent composition of the present invention may be used to prepare lipid nanoparticles to deliver an anionic macromolecule to a cell, in vitro or in vivo. In particular embodiments, the anionic macromolecule is a nucleic acid, which is delivered to a cell using nucleic acid-lipid nanoparticles of the present invention. The methods and transfection reagent composition may be readily adapted for the delivery of any suitable anionic macromolecules for the treatment of any disease or disorder that would benefit from such treatment.

In certain embodiments, the present invention provides methods for introducing a nucleic acid into a cell. Preferred nucleic acids for introduction into cells are siRNA, miRNA, immune-stimulating oligonucleotides, plasmids, antisense and ribozymes. These methods may be carried out by contacting the lipid nanoparticles prepared with the transfection reagent composition of the present invention with the cells for a period of time sufficient for intracellular delivery to occur.

Typical applications include using well known procedures to provide intracellular delivery of siRNA to knock down or silence specific cellular targets. Alternatively applications include delivery of DNA or mRNA sequences that code for therapeutically useful polypeptides. In this manner, therapy is provided for genetic diseases by supplying deficient or absent gene products. Methods of the present invention may be practiced in vitro, ex vivo, or in vivo. For example, the compositions of the present invention can also be used for delivery of nucleic acids to cells in vivo, using methods which are known to those of skill in the art.

The delivery of siRNA by a lipid nanoparticle prepared using the transfection reagent composition of the invention and its effectiveness in silencing gene expression is described below.

For in vivo administration, the pharmaceutical compositions are preferably administered parenterally (e.g., intraarticularly, intravenously, intraperitoneally, subcutaneously, or intramuscularly). In particular embodiments, the pharmaceutical compositions are administered intravenously or intraperitoneally by a bolus injection. Other routes of administration include topical (skin, eyes, mucus membranes), oral, pulmonary, intranasal, sublingual, rectal, and vaginal.

In one embodiment, the present invention provides a method of modulating the expression of a target polynucleotide or polypeptide. These methods generally comprise contacting a cell with a lipid nanoparticle prepared using the transfection reagent of the present invention that is associated with a nucleic acid capable of modulating the expression of a target polynucleotide or polypeptide. As used herein, the term "modulating" refers to altering the expression of a target polynucleotide or polypeptide. Modulating can mean increasing or enhancing, or it can mean decreasing or reducing.

In related embodiments, the present invention provides a method of treating a disease or disorder characterized by overexpression of a polypeptide in a subject, comprising providing to the subject a pharmaceutical composition of the present invention, wherein the anionic macromolecule is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof.

In a further aspect, the invention provides a pharmaceutical composition comprising a lipid nanoparticle prepared using the transfection reagent of the invention and a pharmaceutically acceptable carrier or diluent. Representative pharmaceutically acceptable carriers or diluents include solutions for intravenous injection (e.g., saline or dextrose). The composition can take the form of a cream, ointment, gel, suspension, or emulsion.

The following is a description of a representative transfection reagent composition, lipid nanoparticle system, device and method for making the lipid nanoparticle system using the transfection reagent composition, and method for using a LNP for delivering anionic macromolecules.

Rapid Microfluidic Mixing Allows Production of Monodisperse Lipid Nanoparticles

Formulation of lipid nanoparticles was performed by rapidly mixing a lipid-ethanol solution with an aqueous buffer inside a microfluidic mixer (FIG. 5) designed to induce chaotic advection and provide a controlled mixing environment at intermediate Reynolds number (24<Re<240). The microfluidic channel contains herringbones that generate a chaotic flow by changing the orientation of herringbone structures between half cycles, causing a periodic change in the centers of local rotational and extensional flow.

The following representative transfection reagent composition include an ionizable cationic lipid, 1,17-bis(2-octylcyclopropyl)heptadecan-9-yl-4-(dimethylamino)butanoate (Cationic Lipid A) having an apparent pKa of 6.3 rendering the lipid suitable for encapsulation of siRNA at low pH and providing a near neutral cationic surface charge density at physiological pH. Using the transfection reagent composition as a model system, the choice of surfactant and mol % of the stabilizer on LNP formation by microfluidic mixing was determined. The ethanol solution contained the transfection reagent composition. The aqueous buffer contained siRNA to yield a siRNA/total lipid ratio of 0.06 (wt/wt) and the formed siRNA-LNP was diluted directly into buffer to reduce ethanol content to approximately 22 vol %. siRNA-LNP particle size was dependent on choice of surfactant and the mol % surfactant present in the transfection reagent composition. Particle size decreased with increasing mol % of surfactant in the transfection reagent composition. Increasing the proportion of the surfactant polyoxyethylene (40) stearate in the transfection reagent composition from 1 mol % to 10 mol % decreased resultant siRNA-LNP particle diameter from 103.2 nm to 37.4 nm (Table 1).

Figure 1:
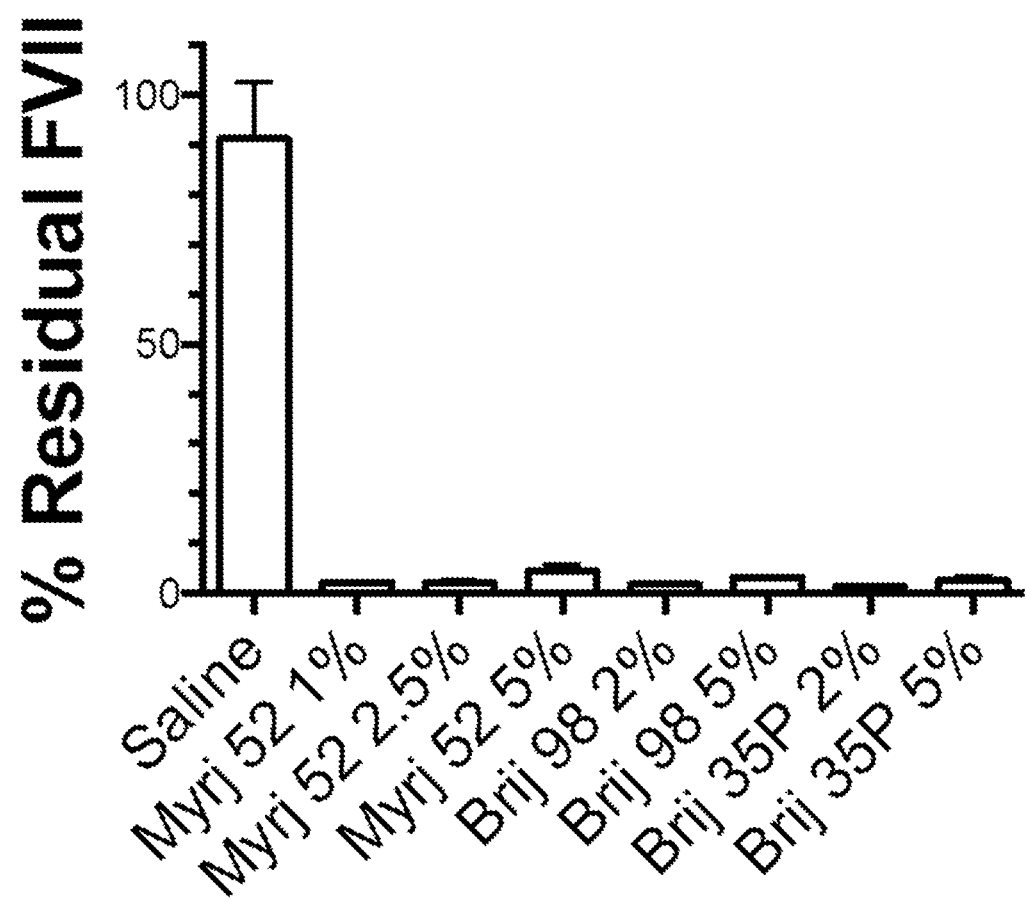
FIG. 1 uses the Factor VII (FVII) Mouse Model to illustrate the in vivo silencing activity of siRNA-LNP prepared with different surfactants (polyoxyethylene (40) stearate (Myrj S40), polyoxyethylene (20) oleyl ether (Brij 98) Brij 35P-polyoxyethylene (23) lauryl ether (Brij 35P)). siRNA-LNP were manufactured using the microfluidic method. Activity was measured as percent Residual FVII protein level as a function of mole percent (mol %) of surfactant used in the siRNA-LNP formulation. All LNP consisted of the following lipid composition according to the formula: 1,17-bis(2-octylcyclopropyl)heptadecan-9-yl-4-(dimethylamino)butanoate: DSPC: Cholesterol: Surfactant (50%:10%:40%-% Surfactant:% Surfactant). siRNA-LNP-to-lipid ratio was 0.06 weight/weight. Mice (n=3) were injected via the tail vein with a single dose equivalent to 1 mg/kg siRNA. Blood collection was performed 24 hours post-injection and FVII levels were determined by colorimetric assay. The data indicates that FVII levels in the blood were reduced by >95% compared to control 24 hours after a single intravenous injection of siRNA-LNP at a siRNA dose of 1 mg/kg. This observation was independent of the surfactant used, or the mol % surfactant incorporated into the siRNA-LNP.

Self-Assembly in a Microfluidic Device can Produce LNP with Near Complete Encapsulation In producing siRNA-LNP systems from transfection reagent composition, a robust process necessarily will provide high percent encapsulation of the OGN product. siRNA encapsulation was evaluated as a function of choice of surfactant and the relevant proportion of the surfactant in the transfection reagent composition. siRNA-LNP formulations achieved percent encapsulation approaching 100 percent independent of surfactant used and relative proportion of surfactant (Table 2).

siRNA-LNP Systems Produced by Microfluidics Using Transfection Reagent Composition can be Highly Potent Gene Silencing Agents In Vivo The ability of siRNA-LNP systems to induce gene silencing in vivo following i.v. injection was investigated using the mouse Factor VII model. Formulations 1,17-bis(2-octylcyclopropyl)heptadecan-9-yl 4-(dimethylamino)butanoate:D SPC:Cholestero 1: Surfactant (50:10:40—% Surfactant: % Surfactant) with a siRNA-to-lipid ratio was 0.06 wt/wt were created using the microfluidic approach. Mice (n=3) were injected via the tail vein with a single dose equivalent to 1 mg/kg siRNA. Blood collection was performed 24 hrs post-injection and FVII levels were determined by colorimetric assay. The data (FIG. 1) indicates that FVII levels in the blood were reduced by >95% compared to control 24 hours after a single intravenous injection equivalent to siRNA dose of 1 mg/kg.

The results demonstrate that a microfluidic device containing a staggered herringbone mixer can be used to generate LNP using transfection reagent compositions varying in lipid compositions, can be used to efficiently encapsulate OGN such as siRNA and that the siRNA-LNPsystems produced exhibit excellent gene silencing capabilities both in vitro and in vivo.

The microfluidics device and system of the invention allow for use of the transfection reagent composition to form LNP, and to form LNP containing OGN of 100 nm size or smaller and provide OGN encapsulation 100%. With regard to formation of LNP, the rate and ratio of mixing are clearly the important parameters. Rapid mixing of the ethanol-lipid solution with aqueous buffer results in an increased polarity of the medium that reduces the solubility of dissolved lipids, causing them to precipitate out of solution and form nanoparticles. Rapid mixing causes the solution to quickly achieve a state of high supersaturation of lipid unimers throughout the entire mixing volume, resulting in the rapid and homogeneous nucleation of nanoparticles. Increased nucleation and growth of nanoparticles depletes the surrounding liquid of free lipid, thereby limiting subsequent growth by the aggregation of free lipid.

Solid Core LNP

LNP structures exhibit limit sizes indicating that ionizable cationic lipid forms inverted micellar structures in the LNP interior. The contribution of the cationic lipid to the electron dense LNP core raises the question of what the molecular structure of such LNP systems may be. It is logical to propose that the cationic lipid, in association with a counter-ion, adopts an inverted structure such as an inverted micelle, consistent with the propensity of these lipids for inverted structures such as the hexagonal $H_{II}$ phase in compositions with anionic lipids. In turn, this would suggest that LNP systems composed of pure cationic lipid should exhibit limit sizes with diameters in the range of 10 nm, which is essentially the thickness of two bilayers surrounding an inverted micelle interior with diameter 2-3 nm. The diameter of the aqueous channels found for phosphatidylethanolamine in the $H_{II}$ phase is 2.6 nm. The microfluidics formulation process provides fast mixing kinetics that drive the generation of limit size systems for LNP systems.

The model provides an understanding of how siRNA encapsulation efficiencies approaching 100% can be achieved during the microfluidic mixing formulation process. This is a major problem for siRNA encapsulation in bilayer systems because, assuming the cationic lipid is equally distributed on both sides of the bilayer, a maximum of 50% siRNA internalization would be expected. The model points to ways in which siRNA-LNP size, composition, and surface charge may be readily modulated. With regard to size, the limit size structure is clearly one that contains one siRNA monomer per particle, suggesting a limit size of approximately 15-20 nm. Such siRNA-LNP particles are readily achieved using microfluidic method of the invention. The limit size siRNA-LNP system consisting of a monomer of siRNA can be potentially used as a building block to achieve siRNA-LNP systems of varying composition and surface charge using microfluidic mixing technology. Rapid mixing of preformed limit size siRNA-LNP with an ethanol solution containing negatively charged lipids, for example, may be expected to result in an interaction with excess cationic lipids to produce internal inverted micellar core structures and a negatively charged surface.

The transfection reagent compositions and lipid nanoparticles of the invention described herein include (i.e., comprise) the components recited. In certain embodiments, the transfection reagent compositions and the lipid nanoparticles of the invention include the recited components and other additional components that do not affect the characteristics of the particles (i.e., the transfection reagent compositions and the lipid nanoparticles consist essentially of the recited components). Additional components that affect the transfection reagent compositions and the lipid nanoparticles' characteristics include components such as additional anionic macromolecules that disadvantageously alter or affect therapeutic profile and efficacy of the particles, additional components that disadvantageously alter or affect the ability of the particles to solubilize the recited anionic macromolecules components, and additional components that disadvantageously alter or affect the ability of the particles to increase the cellular uptake or bioavailability of the recited anionic macromolecules components. In other embodiments, the transfection reagent compositions and the lipid nanoparticles of the invention include only (i.e., consist of) the recited components.

In another aspect, the invention provides kits for preparing lipid nanoparticles. The kits include the transfection reagent composition of the invention. In certain embodiments, the kits include an anionic macromolecule (e.g., nucleic acid). The kits optionally include a device (e.g., microfluidic mixer) for making lipid nanoparticles.

Useful devices for use in the kit include devices described above and those described in WO 2011/140627 and WO 2013/059922, each expressly incorporated herein by reference in its entirety.

In certain embodiments, the device useful in the kit is a device for producing particles at small volumes. As used herein, the term "small volume" refers to volumes less than 2 mL and, in certain embodiments, volumes less than 1 mL (e.g., tens of microliters).

In one embodiment, the device includes:

(a) a first well for receiving a first solution comprising a first solvent;

(b) a first channel in fluid communication with the first well;

(c) a second well for receiving a second solution comprising a second solvent;

(d) a second channel in fluid communication with the second well;

(e) a third channel for receiving first and second streams flowed from the first and second wells through the first and second channels., respectively, wherein the third channel has a first region adapted for flowing the first and second streams introduced into the channel and a second region adapted for mixing the contents of the first and second streams to provide a third stream comprising particles; and (f) a third well for receiving the third stream comprising particles.

This embodiment is illustrated in FIGS. 8, 9, and 12.

The device can include one or more first wells, one or more first channels, one or more second wells, one or more second channels, one or more third channels, and one or more third wells.

In one embodiment, the device further includes means for diluting the third stream to provide a diluted stream comprising stabilized particles.

In another embodiment, the device includes:

(a) a first well for receiving a first solution comprising a first solvent;

(b) a first channel in fluid communication with the first well; and (c) a second well for receiving a second solution comprising a second solvent, wherein the second well further receives a first stream flowed from the first well through the first channel, and wherein the second well is adapted for mixing the contents of the first stream and second solution in the second well to provide a third solution comprising particles.

This embodiment is illustrated in FIGS. 10 and 11.

The device can include one or more first wells, one or more first channels, and one or more second wells.

In certain embodiments, the devices are macrofluidic or microfluidic devices. In certain embodiments, the first and second streams can be mixed by chaotic advection, turbulent mixing, jetting, vortex methods, bubble mixing, micro acoustic streaming, stirring, or other mixing methods. Mixing may be achieved by an active mixing device or passive mixing device. The mixing may occur in a continuous flow format or in defined volume format. The mixing may be achieved using a microfluidic mixer, including a herringbone mixer, zig-zag mixer, micro jet mixer, or micro-vortex mixer. The mixing may be achieved using a macroscopic mixer, including a T-mixer, Y-mixer, or W-mixer.

In certain embodiments, the device is a microfluidic device including one or more microchannels (i.e., a channel having its greatest dimension less than 1 millimeter). In one embodiment, the microchannel has a hydrodynamic diameter from about 20 to about 400 µm. In certain embodiments, the microchannel has two regions: a first region for receiving and flowing at least two streams (e.g., one or more first streams and one or more second streams) into the device. The contents of the first and second streams are mixed in the microchannel's second region. In one embodiment, the second region of the microchannel has a principal flow direction and one or more surfaces having at least one groove or protrusion defined therein, the groove or protrusion having an orientation that forms an angle with the principal direction (e.g., a staggered herringbone mixer), as described in U.S. Patent Application Publication No. 2004/0262223, expressly incorporated herein by reference in its entirety. In one embodiment, the second region of the microchannel comprises bas-relief structures. To achieve maximal mixing rates, it is advantageous to avoid undue fluidic resistance prior to the mixing region. Thus, one embodiment of the invention is a device in which non-microfluidic channels, having dimensions greater than 1000 microns, are used to deliver the fluids to a single mixing channel.

In certain embodiments mixing of the first and second streams can also be accomplished with means for varying the concentration and relative flow rates of the first and second streams. Differing flow rations may be enabled by either differential pressure applied to the flows, differential pressure drops across the flow channels, differential channel impedances, or combination therein, applied to the first and second streams. Differential impedances of the channels through varying the channel heights, widths, lengths, or surface properties, may be used to achieve different flow rates. Fluidic surface tensions, viscosities, and other surface properties of the flows in the one or more first streams and the one or more second streams may be used or considered to achieve different flow rates.

In certain embodiments, the device further includes means for complete or partial purging of the system to minimize the waste volume. After or during manufacture of particles, the device is able to be flown into the one or more first streams and the one or more second streams from the first region of the channel into the second region of the channel a fluid or gas to expel the first stream and second streams. The first and second channel may be fully purged or partially purged under this method. Gasses such as air, nitrogen, argon or others may be used. Liquids including water, aqueous buffer, ethanol, oils, or any other liquid may be used.

In certain embodiments, the device enables backpressures to be applied to ensure the flows of the one or more first streams and the one or more second streams from the first region of the channel into the second region is limited until an initial desired input pressure is achieved. This may be achieved by applying pressure to the outlet channels, negative pressures to the input channels. This may be achieved by loading an outlet reservoir with fluid that may or may not be required in the final particle solution.

In certain embodiments, the device is designed such that fluids are introduced into the device in ways that minimize fluidic waste. This may be achieved by pipetting fluids into the device, pipetting fluids out of the device, connecting the device to syringes, or other methods.

In certain embodiments, the device is microfluidic and produced by soft lithography, the replica molding of microfabricated masters in elastomer. The device has two inlets, one for each of the solutions prepared above, and one outlet. The microfluidic device was produced by soft lithography, the replica molding of microfabricated masters in elastomer. In one example, the device features are 200 µm wide and approximately 70 µm high mixing channel with herringbone structures formed by approximately 25 µm high and 50 µm thick features on the roof of the channel. The device was sealed using an oxygen plasma treatment to a 75×25×1.5 mm glass slide. Other examples, include devices with widths and associated relative dimensions that are smaller (120 µm wide) or larger (300 µm wide). Input and output ports are drilled into the device.

In other embodiments, the device is microfluidic and produced from a hard thermoplastic such as cyclic olefin copolymer. A negative tool is machined using a CNC mill and devices formed using injection molding. Channel dimensions are preserved with the addition of a draft angle ranging between 1° and 5° on vertical surfaces. Molded pieces are sealed to a blank substrate using a variety of techniques, including but not limited to: lamination, solvent welding, heat pressing and combinations thereof. Bonded devices are annealed to remove residual stresses from the production processes. Once formed, devices are installed and used in the custom instrument in the same way as elastomer devices.

To achieve maximal mixing rates it is advantageous to avoid undue fluidic resistance prior to the mixing region. Thus one embodiment the device has non-microfluidic channels, having dimensions greater than 1000 microns, which are used to deliver fluids to a single mixing channel. This device for producing particles includes:

(a) a single inlet channel for receiving a first solution comprising solvent and none or some solution and a second solution comprising particle components in a second solvent; and (b) a second region adapted for mixing the contents of the first and second streams to provide a third stream comprising particles.

In such an embodiment, the first and second streams are introduced into the channel by a single inlet or by one or two channels not having micro-dimensions, for example, a channel or channels having dimensions greater than 1000 µm (e.g., 1500 or 2000 µm or larger). These channels may be introduced to the inlet channel using adjacent or concentric macrosized channels.

The following examples are provided for the purpose of illustrating, not limiting, the claimed invention.

EXAMPLES

Materials 1,2-distearoyl-sn-glycero-3-phosphocholine (DSPC) and cholesterol were obtained from Avanti Polar Lipids (Alabaster, Ala.). 4-(2-Hydroxyethyl)piperazine-1-ethanesulfonic acid (HEPES), cholesterol and surfactants were obtained from Sigma (St. Louis, Mo.). (Fair Lawn, N.J.). RNase A was obtained from Applied Biosystems/Ambion (Austin, Tex.). Factor VII (FVII) targeting, and low GC negative control siRNA were purchased from Invitrogen (Carlsbad, Calif.). Factor VII siRNA: 5'-GGAUCAUCUCAAGUC-UUACTT-3' [SEQ ID NO: 1] (FVII sense), and 5'-GUAAGACUUGAGAUGAUCCTT-3' [SEQ ID NO: 2] (FVII antisense). 1,17-bis(2-octylcyclopropyl)heptadecan-9-yl-4-(dimethylamino)butanoate was synthesized by AlCana Technologies Inc. (Vancouver, BC).

Example 1

Preparation of LNP Systems

In the example, the preparation of an siRNA-LNP system using the preformed vesicle method is described.

siRNA-LNP systems were made using the preformed vesicle method as described in N. Maurer, K. F. Wong, H. Stark, L. Louie, D. McIntosh, T. Wong, P. Scherrer, S. Semple and P. R. Cullis, "Spontaneous Entrapment of Polynucleotides Upon Electrostatic Interaction With Ethanol Destabilized Cationic Liposomes: Formation of Small Multilamellar Liposomes," *Biophys. J.* 80:2310-2326 (2001). Cationic lipid, DSPC, cholesterol and PEG-lipid were first solubilized in ethanol at the appropriate molar ratio. The lipid composition was then added dropwise to an aqueous buffer (citrate or acetate buffer, pH 4) while vortexing to a final ethanol and lipid concentration of 30% (v/v). The hydrated lipids were then extruded five times through two stacked 80 nm pore-sized filters (Nuclepore) at room temperature using a Lipex Extruder (Northern Lipids, Vancouver, Canada). The siRNA (solubilized in an identical aqueous solution containing 30% ethanol) was added to the vesicle suspension while mixing. A target siRNA/lipid ratio of 0.06 (wt/wt) was generally used. This composition was incubated for 30 minutes at 35° C. to allow vesicle reorganization and encapsulation of the siRNA. The ethanol was then removed and the external buffer replaced with phosphate-buffered saline (PBS) by dialysis (12-14 k MW cut-off, Spectrum medical instruments) to 50 mM citrate buffer, pH 4.0 and then dialysis to PBS, pH 7.4.

Example 2

Preparation of LNP Systems

In the example, a representative transfection reagent composition used to prepare a siRNA-LNP system of the invention using a microfluidic staggered herringbone mixer is described.

siRNA-LNP Preparation

Oligonucleotide (siRNA) solution was prepared in 25 mM acetate buffer at pH 4.0. Depending on the desired oligonucleotide-to-lipid ratio and formulation concentration, solutions were prepared at a target concentration of 0.3 mg/ml to 1.9 mg/ml total lipid. A lipid solution containing 1,17-bis(2-octylcyclopropyl)heptadecan-9-yl 4-(dimethylamino)butanoate, DSPC, cholesterol, and a surfactant at the appropriate molar ratio was prepared in ethanol and diluted with 25 mM acetate buffer to achieve an ethanol concentration of 90% (v/v). FIG. 5 is a schematic illustration of the microfluidic apparatus used in this example. The device has two inlets, one for each of the solutions prepared above, and one outlet. The microfluidic device was produced by soft lithography, the replica molding of microfabricated masters in elastomer. The device has two inlets, one for each of the solutions prepared above, and one outlet. The microfluidic device was produced by soft lithography, the replica molding of microfabricated masters in elastomer. The device features a 300 µm wide and approximately 130 µm high mixing channel with herringbone structures formed by approximately 40 µm high and 75 µm thick features on the roof of the channel. The device was sealed using an oxygen plasma treatment to a 40×36×2 mm glass slide with three 1.5 mm holes drilled to match the inlet and outlet ports of the device. The bonded device was installed into a custom instrument, having a top plate with o-rings to seal the device to the instrument, and a back plate with luer fitting for loading reagents in syringes. Once the device and reagents were loaded, the instrument acted as a syringe pump to dispense the fluid at the prescribed rate through the device. The flow rate of each stream was varied from 0.1 ml/min to 20 ml/min. The instrument introduces the two solutions into the microfluidic device, where they come into contact at a Y-junction. Insignificant mixing occurs under laminar flow by diffusion at this point, whereas the two solutions become mixed as they pass along the herringbone structures and around the serpentine channels.

Mixing occurs in these structures by chaotic advection, causing the characteristic separation of laminate streams to become increasingly small, thereby promoting rapid diffusion. This mixing occurs on a millisecond time scale and results in the lipids being transferred to a progressively more aqueous environment, reducing their solubility and resulting in the spontaneous formation of LNP. By including cationic lipids in the transfection reagent composition, entrapment of oligonucleotide species is obtained through association of the positively charged lipid head group and negatively charged oligonucleotide. Following mixing in the microfluidic device, the LNP composition was generally diluted into a glass vial containing two volumes of stirred buffer. Ethanol is finally removed through dialysis to 50 mM citrate buffer, pH 4.0 and then dialysis to PBS, pH 7.4. Empty vesicles were similarly produced, with the oligonucleotide absent from the buffer solution.

LNP Characterization

Particle size was determined by dynamic light scattering using a Nicomp model 370 Submicron Particle Sizer (Particle Sizing Systems, Santa Barbara, Calif.). Number-weighted and intensity-weighted distribution data was used. Lipid concentrations were verified by measuring total cholesterol using the Cholesterol E enzymatic assay from Wako Chemicals USA (Richmond, Va.). Removal of free siRNA was performed with VivaPureDMiniH columns (Sartorius Stedim Biotech GmbH, Goettingen, Germany). The eluents were then lysed in 75% ethanol and siRNA was quantified by measuring absorbance at 260 nm. Encapsulation efficiency was determined from the ratio of oligonucleotide before and after removal of free oligonucleotide content, normalized to lipid content.

In Vivo Activity of siRNA-LNP for FVII Activity

Six to eight week old, female C57Bl/6 mice were obtained from Charles River Laboratories. siRNA-LNP containing Factor VII siRNA were filtered through a 0.2 µm filter and diluted to the required concentrations in sterile phosphate buffered saline prior to use. The formulations were administered intravenously via the lateral tail vein at a volume of 10 ml/kg. After 24 h, animals were anaesthetized with Ketamine/Xylazine and blood was collected by cardiac puncture. Samples were processed to serum (Microtainer Serum Separator Tubes; Becton Dickinson, N.J.) and tested immediately or stored at −70° C. for later analysis of serum Factor VII levels. All procedures were performed in accordance with local, state, and federal regulations as applicable and approved by the Institutional Animal Care and Use Committee (IACUC).

Serum Factor VII levels were determined using the colorimetric Biophen VII assay kit (Anaira). Control serum was pooled and serially diluted (200%-3.125%) to produce a calibration curve for calculation of FVII levels in treated animals. Appropriately diluted plasma samples from treated animals (n=3 per dosage) and a saline control group (n=4) were analyzed using the Biophen VII kit according to manufacturer's instructions. Analysis was performed in 96-well, flat bottom, non-binding polystyrene assay plates (Corning, Corning, N.Y.) and absorbance was measured at 405 nm. Factor VII levels in treated animals were determined from a calibration curve produced with the serially diluted control serum.

Example 3

Preparation and Characteristics of a Representative Lipid Nanoparticle Using a Transfection Reagent Composition In this example, a representative transfection reagent compositions of the invention, was used to prepare a representative siRNA-LNP of the invention is described.

The siRNA solution was prepared at 0.67 mg/mL in 25 mM acetate buffer, pH 4.0. The lipid solution was prepared to contain 1,17-bis(2-octylcyclopropyl)heptadecan-9-yl-4-(dimethylamino)butanoate: DSPC: cholesterol: Surfactant-Mryj 52 (50:10:37.5:2.5 mol %) at a concentration of 19.82 mg/mL in ethanol. The siRNA-to-lipid ratio was 0.07 (wt/wt). Each solution was input into the microfluidic mixer at a flow rate ratio of 3:1 aqueous:ethanol and a total flow rate of 12 mL/min resulting in a final ethanol concentration of 25 vol %. Ethanol was removed by dialysis with MES Citrate pH 6.7 (1:500 dilution). The final siRNA-LNP was prepared by further dialysis in phosphate-buffered saline (PBS) pH 7.4.

Particle size was determined by dynamic light scattering using a Malvern ZetasizerNanoZS (Malvern Instruments, Westborough, Mass., USA). Sample measurement was performed in PBS pH 7.4 and intensity-weighted distribution data was used. The particles had a mean particle diameter of 49.7 nm, with a polydispersity index (PDI)=0.06.

While illustrative embodiments have been illustrated and described, it will be appreciated that various changes can be made therein without departing from the spirit and scope of the invention.

The embodiments of the invention in which an exclusive property or privilege is claimed are defined as follows:

1. A kit for preparing a lipid nanoparticle, the kit comprising:
 a transfection reagent composition comprising:
  (a) 1,17-bis(2-octylcyclopropyl)heptadecan-9-yl-4-(dimethylamino)butanoate, or a pharmaceutically acceptable salt thereof;
  (b) 1,2-distearoyl-sn-glycero-3-phosphocholine (DSPC);
  (c) cholesterol; and
  (d) one or more surfactants selected from polyoxyethylene (20) oleyl ether, polyoxyethylene (23) lauryl ether, or polyoxyethylene (40) stearate; and
 a device for making lipid particles, wherein the device comprises:
  (a) a first well for receiving a first solution comprising a first solvent;
  (b) a first channel in fluid communication with the first well;
  (c) a second well for receiving a second solution comprising a second solvent;
  (d) a second channel in fluid communication with the second well;
  (e) a third channel for receiving first and second streams flowed from the first and second wells through the first and second channels, respectively, wherein the third channel has a first region adapted for flowing the first and second streams introduced into the channel and a second region adapted for mixing the contents of the first and second streams to provide a third stream comprising particles, and wherein the second region is configured to mix the contents of the first and second streams by inducing chaotic advection; and
  (f) a third well for receiving the third stream comprising particles,
 wherein the first channel and the second channel have different channel impedances.

\* \* \* \* \*

SEQUENCE LISTING

<160> NUMBER OF SEQ ID NOS: 2

<210> SEQ ID NO 1
<211> LENGTH: 21
<212> TYPE: DNA
<213> ORGANISM: Artificial sequence
<220> FEATURE:
<223> OTHER INFORMATION: Synthetic

<400> SEQUENCE: 1
ggaucaucuc aagucuuact t          21

<210> SEQ ID NO 2
<211> LENGTH: 21
<212> TYPE: DNA
<213> ORGANISM: Artificial sequence
<220> FEATURE:
<223> OTHER INFORMATION: Synthetic

<400> SEQUENCE: 2
guaagacuug agaugaucct t          21